(12) United States Patent
Blanco Arbués et al.

(10) Patent No.: US 9,952,218 B2
(45) Date of Patent: Apr. 24, 2018

(54) METHODS FOR IDENTIFYING HIV NEUTRALIZING ANTIBODIES

(71) Applicants: LABORATORIOS DEL DR. ESTEVE S.A., Barcelona (ES); FUNDACIÓ PRIVADA INSTITUT DE RECERCA DE LA SIDA—CAIXA, Badalona (ES)

(72) Inventors: Julián Miguel Blanco Arbués, Vic (ES); Jorge Carrillo Molina, Badalona (ES)

(73) Assignees: LABORATORIOS DEL DR. ESTEVE S.A., Barcelona (ES); FUNDACIÓ PRIVADA INSTITUT DE RECERCA DE LA SIDA—CAIXA, Badalona (ES)

(*) Notice: Subject to any disclaimer, the term of this patent is extended or adjusted under 35 U.S.C. 154(b) by 0 days.

(21) Appl. No.: 14/426,235

(22) PCT Filed: Sep. 6, 2013

(86) PCT No.: PCT/EP2013/068446
§ 371 (c)(1),
(2) Date: Mar. 5, 2015

(87) PCT Pub. No.: WO2014/037490
PCT Pub. Date: Mar. 13, 2014

(65) Prior Publication Data
US 2015/0233924 A1    Aug. 20, 2015

(30) Foreign Application Priority Data
Sep. 6, 2012 (EP) .................... 12382342

(51) Int. Cl.
*G01N 33/577* (2006.01)
*C07K 14/005* (2006.01)
*G01N 33/569* (2006.01)
*C07K 16/10* (2006.01)
*C12N 7/00* (2006.01)

(52) U.S. Cl.
CPC ..... *G01N 33/56988* (2013.01); *C07K 14/005* (2013.01); *C07K 16/1063* (2013.01); *C12N 7/00* (2013.01); *C07K 2317/14* (2013.01); *C07K 2317/34* (2013.01); *C07K 2317/76* (2013.01); *C07K 2319/30* (2013.01); *C12N 2740/16122* (2013.01); *G01N 2333/162* (2013.01)

(58) Field of Classification Search
CPC ............ C07K 14/005; C07K 14/70514; C07K 2319/00; C07K 14/705; C07K 14/70535; C07K 16/1063; C07K 2317/56; C07K 2317/622; C07K 16/2812; C07K 16/283; C07K 2319/74; C07K 2317/76; C07K 16/1045; C07K 2317/569; C07K 2319/30; C07K 16/005; C07K 2316/96; C07K 2317/53; C07K 2319/32; C07K 2317/55; C07K 2317/33; C07K 16/10; C12N 7/00; C12N 2740/16011; C12N 2740/16111; G01N 33/56988; G01N 2333/162; G01N 2500/04; G01N 2333/16; G01N 2333/161; G01N 33/6854; G01N 33/505; G01N 33/5052; G01N 2333/70514; A61K 2039/505; A61K 38/1774; A61K 39/21; A61K 2207/15; A61K 2217/072
See application file for complete search history.

(56) References Cited

U.S. PATENT DOCUMENTS 5,091,513 A   2/1992   Huston

FOREIGN PATENT DOCUMENTS

WO   WO 03/040311    5/2003
WO   WO 2011/146891  11/2011

OTHER PUBLICATIONS

Montefiori, "Neutralizing antibodies against HIV-1: can we elicit them with vaccines and how much do we need?", Curr Opin HIV AIDS, 2009, 4(5):347-351.*
Zettlmeissl et al. DNA and Cell Biology, 1990, vol. 9, No. 5, pp. 347-353.*
Meyuhas et al. Molecular Immunology 2005, vol. 42, No. 9, pp. 1099-1109.*
Anthony et al. J. Virology, online Oct. 28, 2009, or published as Journal on Jan. 2010, vol. 84, No. 1, pp. 261-269.*
Allaway et al. AIDS research and human retroviruses, 1995, vol. 11, No. 5, pp. 533-539.*
Abela, et al., Curent Pharmaceutical Design, vol. 16, p. 3754-3766, 2010.
Altschul, et al., Journal Mol. Biol., vol. 215, p. 403-410, 1990.
Altschul, et al., Methods in Enzymology, vol. 266, No. 27, p. 460-480, 1990.
Altschul, et al., Nucleic Acids Research, vol. 25, No. 17, p. 3389-3402, 1997.
Auer, Nature Biotechnology, vol. 24, No. 1, p. 41-43, Jan. 2006.
Barbas, et al., Proc. Natl. Acad. Sci. USA, vol. 89, p. 9339-9343, Oct. 1992.
Blanco, et al., Journal of Leukocyte Biology, vol. 76, p. 804-811, Oct. 2004.

(Continued)

*Primary Examiner* — Bao Li

(74) *Attorney, Agent, or Firm* — Hueschen and Sage

(57) ABSTRACT

The present invention relates to an in vitro method for determining HIV neutralizing antibodies in a sample. It further relates to a fusion protein to be used in said method and a nucleic acid encoding said fusion protein.

14 Claims, 8 Drawing Sheets

(56) References Cited

OTHER PUBLICATIONS

Blanco, et al., Virology, vol. 305, p. 318-329, 2003.
Chen, et al., Antiviral Research, vol. 88, p. 107-115, 2010.
Chen, et al., Journal of Virology, vol. 85, No. 18, p. 9395-9405, Sep. 2011.
Feng, et al., Biochemistry, vol. 39, p. 15399-15409, May 11, 2000.
Hessell, et al., Nature Medicine, vol. 15, No. 8, p. 951-954, Aug. 2009.
Hessell, et al., Nature, vol. 449, Letters, Sep. 6, 2007.
Humphreys, et al., Protein Expression and Purification, vol. 20, p. 252-264, 2000.
Huston, et al., Proc. Natl. Acad. Sci. USA, vol. 85, Biochemistry, p. 5879-5883, Aug. 1988.
International Search Report for PCT/EP2013/068446 dated Sep. 26, 2013.
Karlin, et al., Proc. Natl. Acad. Sci. USA, vol. 90, Evolution, p. 5873-5877, Jun. 1993.
Karlin, et al., Proc. Natl. Acas. Sci. USA, vol. 87, Evolution, p. 2264-2268, Mar. 1990.
Li, et al., Journal of Virology, vol. 79, No. 16, p. 10108-10125, Aug. 2005.
Li, et al., Nat. Med., vol. 13, No. 9, p. 1032-1034, Sep. 2007.
Lynch, Journal of Virology, vol. 86, No. 14, p. 7588-7595, Jul. 2012.
Mascola, et al., Annu. Rev. Immunol. vol. 28, p. 413-444, 2010.
Montefiori, Current Protocols in Immunology, Unit 12.11, Chapter 12, Jan. 2005.
Montefiroi, et al., Current Opinion in HIV and AIDS, vol. 4, p. 347-351, 2009.
Moulard, PHAS, vol. 99, No. 10, p. 6913-6918, May 14, 2002.
Muster, et al., Journal of Virology, vol. 67, No. 11, p. 6642-6647, Nov. 1993.
Narum, et al, Infection and Immunity, vol. 69, No. 12, p. 7250-7253, Dec. 2001.
Needleman, et al., Journal Mol. Biol. vol. 48, p. 443-453, 1970.
Outchkourov, et al., Protein Expression and Purificaiton, vol. 24, p. 18-24, 2002.
Pearson, et al., Proc. Natl. Acad. Sci. USA, vol. 85, pp. 2444-2448, Apr. 1988.
Pietzsch, et al. Journal Exp. Med., vol. 207, No. 9, p. 1995-2002, Aug. 2, 2010.
Sanchez-Palomino, et al., Vaccine, vol. 29, p. 5250-5259, 2011.
Sanger, et al., Proc. Natl. Acad. Sci. USA, vol. 74, No. 12, Biochemistry, p. 5463-5467, Dec. 1977.
Scanlan, et al., Journal of Virology, vol. 76, No. 14, p. 7306-7321, Jul. 2002.
Scheid, et al., Science, 333(6049), p. 1633-1637, Sep. 16, 2011.
Smith, et al., Advance in Applied Mathematics 2, p. 482-489, 1981.
Sterjovski, et al., Virology, vol. 410, p. 418-428, 2011.
Tomaras, et al., Journal of Virology, vol. 82, No. 24, p. 12449-12463, Dec. 2008.
Veazey, et al., Nature Medicine, vol. 9, No. 3, p. 343-346, Mar. 2003.
Walker, et al., Nature, 477(7365), p. 466-470, Sep. 22, 2011.
Walker, et al., Science, 326(5950), pg. 285-289, Oct. 2009.
Wei, et al., Nature, vol. 422, p. 307-312, Mar. 20, 2003.
Wu, et al., Science, vol. 329(5993), p. 856-861, Aug. 13, 2010.
Zwick, et al., Journal of Virology, vol. 75, No. 22, p. 10892-10905, Nov. 2001.
Wu, et el., Science, 2010, 329, 896-661.
Diskin, et al., Nature Structural & Molecular Biology 17, 608-613 (2010).

* cited by examiner

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: CD4 L sense primer

<400> SEQUENCE: 1
caccatgaac cggggagtcc cttttag                                27

<210> SEQ ID NO 2
<211> LENGTH: 29
<212> TYPE: DNA
<213> ORGANISM: Artificial Sequence
<220> FEATURE:
<223> OTHER INFORMATION: CD4L AS NheI primer

<400> SEQUENCE: 2
tattagctag caccacgatg tctattttg                              29

<210> SEQ ID NO 3
<211> LENGTH: 40
<212> TYPE: DNA
<213> ORGANISM: Artificial Sequence
<220> FEATURE:
<223> OTHER INFORMATION: MPER-mIgG1-S primer

<400> SEQUENCE: 3
gaatagagct ggtgggctag ctgtgcccag ggattgtggt                  40

<210> SEQ ID NO 4
<211> LENGTH: 31
<212> TYPE: DNA
<213> ORGANISM: Artificial Sequence
<220> FEATURE:
<223> OTHER INFORMATION: mIgG1-AS primer

<400> SEQUENCE: 4
ttattctcga gtcatttacc aggagagtgg g                           31

<210> SEQ ID NO 5
<211> LENGTH: 609
<212> TYPE: DNA
<213> ORGANISM: Artificial Sequence
<220> FEATURE:
<223> OTHER INFORMATION: Fragment of the huCD4mIgG1 fusion protein
      nucleotide sequence

<400> SEQUENCE: 5
atgaaccggg gagtcccttt taggcacttg cttctggtgc tgcaactggc gctcctccca    60
gcagccactc agggaaagaa agtggtgctg ggcaaaaaag gggatacagt ggaactgacc   120
tgtacagctt cccagaagaa gagcatacaa ttccactgga aaaactccaa ccagataaag   180
attctgggaa atcagggctc cttcttaact aaaggtccat ccaagctgaa tgatcgcgct   240
gactcaagaa gaagcctttg ggaccaagga aacttccccc tgatcatcaa gaatcttaag   300
atagaagact cagatactta catctgtgaa gtggaggacc agaaggagga ggtgcaattg   360
ctagtgttcg gattgactgc caactctgac acccacctgc ttcaggggca gagcctgacc   420
ctgaccttgg agagcccccc tggtagtagc ccctcagtgc aatgtaggag tccaaggggt   480
aaaaacatac aggggggaa gaccctctcc gtgtctcagc tggagctcca ggatagtggc   540

```
acctggacat gcactgtctt gcagaaccag aagaaggtgg agttcaaaat agacatcgtg      600
gtgctagct                                                             609

<210> SEQ ID NO 6
<211> LENGTH: 690
<212> TYPE: DNA
<213> ORGANISM: Artificial Sequence
<220> FEATURE:
<223> OTHER INFORMATION: Fragment of the huCD4mIgG1 fusion protein
      nucleotide sequence

<400> SEQUENCE: 6
gtgcccaggg attgtggttg taagccttgc atatgtacag tcccagaagt atcatctgtc       60
ttcatcttcc ccccaaagcc caaggatgtg ctcaccatta ctctgactcc taaggtcacg      120
tgtgttgtgg tagacatcag caaggatgat cccgaggtcc agttcagctg gtttgtagat      180
gatgtggagg tgcacacagc tcagacgcaa ccccgggagg agcagttcaa cagcactttc      240
cgctcagtca gtgaacttcc catcatgcac caggactggc tcaatggcaa ggagttcaaa      300
tgcagggtca acagtgcagc tttccctgcc cccatcgaga aaaccatctc caaaaccaaa      360
ggcagaccga aggctccaca ggtgtacacc attccacctc ccaaggagca gatggccaag      420
gataaagtca gtctgacctg catgataaca gacttcttcc ctgaagacat tactgtggag      480
tggcagtgga atgggcagcc agcggagaac tacaagaaca ctcagcccat catggacaca      540
gatggctctt acttcgtcta cagcaagctc aatgtgcaga gagcaactg ggaggcagga      600 aatactttca cctgctctgt gttacatgag ggcctgcaca accaccatac tgagaagagc      660
ctctcccact ctcctggtaa atgactcgag                                      690

<210> SEQ ID NO 7
<211> LENGTH: 430
<212> TYPE: PRT
<213> ORGANISM: Artificial Sequence
<220> FEATURE:
<223> OTHER INFORMATION: CD4-Fc fusion protein

<400> SEQUENCE: 7

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160
```

```
Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Val Pro Arg Asp Cys
        195                 200                 205

Gly Cys Lys Pro Cys Ile Cys Thr Val Pro Glu Val Ser Ser Val Phe
    210                 215                 220

Ile Phe Pro Pro Lys Pro Lys Asp Val Leu Thr Ile Thr Leu Thr Pro
225                 230                 235                 240

Lys Val Thr Cys Val Val Asp Ile Ser Lys Asp Asp Pro Glu Val
            245                 250                 255

Gln Phe Ser Trp Phe Val Asp Asp Val Glu Val His Thr Ala Gln Thr
            260                 265                 270

Gln Pro Arg Glu Glu Gln Phe Asn Ser Thr Phe Arg Ser Val Ser Glu
        275                 280                 285

Leu Pro Ile Met His Gln Asp Trp Leu Asn Gly Lys Glu Phe Lys Cys
        290                 295                 300

Arg Val Asn Ser Ala Ala Phe Pro Ala Pro Ile Glu Lys Thr Ile Ser
305                 310                 315                 320

Lys Thr Lys Gly Arg Pro Lys Ala Pro Gln Val Tyr Thr Ile Pro Pro
                325                 330                 335

Pro Lys Glu Gln Met Ala Lys Asp Lys Val Ser Leu Thr Cys Met Ile
            340                 345                 350

Thr Asp Phe Phe Pro Glu Asp Ile Thr Val Glu Trp Gln Trp Asn Gly
            355                 360                 365

Gln Pro Ala Glu Asn Tyr Lys Asn Thr Gln Pro Ile Met Asp Thr Asp
        370                 375                 380

Gly Ser Tyr Phe Val Tyr Ser Lys Leu Asn Val Gln Lys Ser Asn Trp
385                 390                 395                 400

Glu Ala Gly Asn Thr Phe Thr Cys Ser Val Leu His Glu Gly Leu His
                405                 410                 415

Asn His His Thr Glu Lys Ser Leu Ser His Ser Pro Gly Lys
            420                 425                 430

<210> SEQ ID NO 8
<211> LENGTH: 203
<212> TYPE: PRT
<213> ORGANISM: Artificial Sequence
<220> FEATURE:
<223> OTHER INFORMATION: CD4 fragment

<400> SEQUENCE: 8

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95
```

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
        180                 185                 190

Val Glu Phe Lys Ile Asp Ile Val Val Leu Ala
        195                 200

<210> SEQ ID NO 9
<211> LENGTH: 227
<212> TYPE: PRT
<213> ORGANISM: Artificial Sequence
<220> FEATURE:
<223> OTHER INFORMATION: Fc fragment

<400> SEQUENCE: 9

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225

<210> SEQ ID NO 10
<211> LENGTH: 1293

```
<212> TYPE: DNA
<213> ORGANISM: Artificial Sequence
<220> FEATURE:
<223> OTHER INFORMATION: Sequence encoding CD4-Fc fusion protein

<400> SEQUENCE: 10
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aacttccccc tgatcatcaa gaatcttaag     300
atagaagact cagatactta catctgtgaa gtggaggacc agaaggagga ggtgcaattg     360
ctagtgttcg gattgactgc caactctgac acccacctgc ttcaggggca gagcctgacc     420
ctgaccttgg agaccccccc tggtagtagc ccctcagtgc aatgtaggag tccaaggggt     480
aaaaacatac aggggggaa gaccctctcc gtgtctcagc tggagctcca ggatagtggc     540
acctggacat gcactgtctt gcagaaccag aagaaggtgg agttcaaaat agacatcgtg     600
gtgctagctg tgcccaggga ttgtggttgt aagccttgca tatgtacagt cccagaagta     660
tcatctgtct tcatcttccc cccaaagccc aaggatgtgc tcaccattac tctgactcct     720
aaggtcacgt gtgttgtggt agacatcagc aaggatgatc ccgaggtcca gttcagctgg     780
tttgtagatg atgtggaggt gcacacagct cagacgcaac cccgggagga gcagttcaac     840
agcactttcc gctcagtcag tgaacttccc atcatgcacc aggactggct caatggcaag     900
gagttcaaat gcagggtcaa cagtgcagct ttccctgccc ccatcgagaa aaccatctcc     960
aaaaccaaag gcagaccgaa ggctccacag gtgtacacca ttccacctcc caaggagcag    1020
atggccaagg ataaagtcag tctgacctgc atgataacag acttcttccc tgaagacatt    1080
actgtggagt ggcagtggaa tgggcagcca gcggagaact acaagaacac tcagcccatc    1140
atggacacag atggctctta cttcgtctac agcaagctca atgtgcagaa gagcaactgg    1200
gaggcaggaa atactttcac ctgctctgtg ttacatgagg gcctgcacaa ccaccatact    1260
gagaagagcc tctcccactc tcctggtaaa tga                                 1293
```

METHODS FOR IDENTIFYING HIV NEUTRALIZING ANTIBODIES

FIELD OF THE INVENTION

The present invention refers to an in vitro method for identifying HIV neutralizing antibodies in a sample. The invention also relates to a fusion protein to be used in said method and the nucleic acid encoding said fusion protein.

BACKGROUND OF THE INVENTION

During the course of an infection process the organism develops a broad humoral response directed against different pathogen's antigens which, in conjunction with the innate and T-cell responses, control the infection and preserve the integrity of the organism. In the setting of the HIV-1 infection, this humoral response can be detected early during the infection but it is known to be ineffective, mainly because the antibodies produced by most patients recognize viral epitopes which cannot interfere with the replicative cycle of the virus. See Tomaras G, et al., J. Virol. 2008; 82:12449-12463. In fact, antibodies with the capacity to neutralize the autologous virus can be identified after few months only in some patients; and several years are required to develop broadly neutralizing antibodies (bnAbs). See Mascola J, et al., Annu. Rev. Immunol. 2010; 28:413-444. To date, only a few broadly neutralizing antibodies have been identified and all of them recognize a set of conserved epitopes in the envelope protein with an important role in viral fitness. These antibodies include anti-CD4 binding site (CD4bs) antibodies (IgGb12 and VCR01), anti-CD4 induced-epitope antibodies (X5), anti-gp41 antibodies (2F5 and 4E10), anticarbohydrates (2G12), anti-glycosylated quaternary epitopes (PG9 and PG16) and anti-core antibodies. See Barbas C, et al., Proc. Natl. Acad. Sci USA 1992; 89:9339-9343, Wu X, et al., Science 2010; 329: 856-861, Moulard M, et al., Proc. Natl. Acad. Sci. USA 2002; 99:6913-6918, Muster T, et al., J. Virol. 1993; 67:6642-6647, Zwick M, et al., J. Virol. 2001; 75:10892-10905, Scanlan C, et al., J. Virol. 2002; 76:7306-7321, Walker L, et al., Science 2009; 326:285-289, and Pietzsch J, et al., J. Exp. Med. 2010; 207:1995-2002. Among them, antibodies that can block the interaction of gp120/CD4 such as anti-CD4bs antibodies can be highlighted for several reasons: 1) they recognize a conserved region of gp120, 2) they can neutralize a broad number of viral isolates and 3) they can prevent or control the infection as it has been shown in animal models of HIV-1 infection. See Hessell A, et al., Nat. Med. 2009; 15:951-954, Hessell A, et al., Nature 2007; 449:101-104, and Veazey R, et al., Nat. Med. 2003; 9:343-346. Therefore, the elicitation of this sort of bnAbs is an interesting goal for any vaccination strategy. However, one of the major handicaps in the study of these antibodies is their identification. Broadly neutralizing antibodies in general, and CD4bs antibodies in particular, recognize conformational epitopes which are difficult to mimic in vitro. To date, several strategies have been followed to study CD4bs antibodies, including the use of recombinant proteins and mutant variants which are differentially recognized by these antibodies. See Li Y, et al., Nat. Med. 2007; 13:1032-1034, and Lynch R, et al., J. Virol. 2012; 86(4):7588-7595, and Wu, 2010, supra. In addition, a cell-to-cell viral transfer assay was recently developed which allows detecting the presence of CD4/gp120 blocking antibodies in plasma samples. This assay is based on the viral entrance process, which is completely inhibited in the presence of antibodies that block the gp120/CD4 interaction like CD4bs or anti-CD4 antibodies. By definition any antibody which is able to block the interaction between gp120 and the CD4 receptor might be a neutralizing antibody. Furthermore, this approach showed a strong correlation between the presence of gp120/CD4 blocking antibodies and the neutralizing capacity of the plasma. See Sanchez-Palomino S, et al., Vaccine 2011; 29:5250-5259. More recently, it has been shown that more than 80% of HIV-1 infected patients can develop CD4bs antibodies, indicating that this reactivity might be more frequent than it has been previously described. See Lynch, 2012, supra.

However, no clear correlation between the presence of these antibodies and the neutralizing capacity of the plasma samples could be established in this case. These discrepancies highlight that the methodology is an important issue to take into account before planning the analysis of gp120/CD4 blocking antibodies. There is a need in the art for more rapid and reliable methods for identifying HIV neutralizing antibodies.

SUMMARY OF THE INVENTION

In a first aspect, the invention relates to an in vitro method for determining HIV neutralizing antibodies in a sample, comprising:
(i) contacting a cell comprising the CD4 binding site of gp120 on its surface with said sample and with a fusion protein comprising (i) a protein capable of binding to the CD4 binding-site of gp120 and (ii) a Fc region of a primary antibody, and
(ii) measuring the binding efficacy of said fusion protein to the CD4 binding site of gp120,
wherein HIV neutralizing antibodies are determined in said sample if said binding is inhibited in the presence of the sample.

In a second aspect, the present invention relates to a fusion protein comprising (i) a protein capable of binding to the CD4 binding-site of gp120 and (ii) a Fc region of a primary antibody.

In a third aspect, the invention relates to a nucleic acid encoding the fusion protein of the second aspect and to an expression cassette, or a vector comprising said nucleic acid.

In a fourth aspect, the invention relates to a kit comprising the (i) fusion protein of the second aspect, the nucleic acid, the vector or the transgenic cell of the third aspect and (ii) a reporter capable of binding to said fusion protein.

In another aspect, the invention relates to an in vitro method for the identification of an antibody-producing cell expressing HIV neutralizing antibodies, comprising:
(i) contacting a cell comprising the CD4 binding site of gp120 on its surface with a supernatant of a culture of said antibody-producing cells and with a fusion protein comprising (i) a protein capable of binding to the CD4 binding-site of gp120 and (ii) a Fc region of a primary antibody, and
(ii) measuring the binding efficacy of said fusion protein to the CD4 binding site of gp120,
wherein the antibody-producing cell are determined as expressing HIV neutralizing antibodies if said binding inhibited in the presence of said supernatant.

In another aspect, the invention relates to a method for producing HIV neutralizing antibodies, comprising:
(i) culturing antibody-producing cells isolated according to the method of the invention, and
(ii) isolating the antibodies expressed by said antibody-producing cells.

In yet another aspect, the invention relates to HIV-neutralizing antibodies produced using a method according to the invention or by antibody-producing cells identified by a method according to any of claims for use in the treatment or prevention of a disease associated with HIV infection.

DEPOSIT OF MICROORGANISMS

Figure 1:
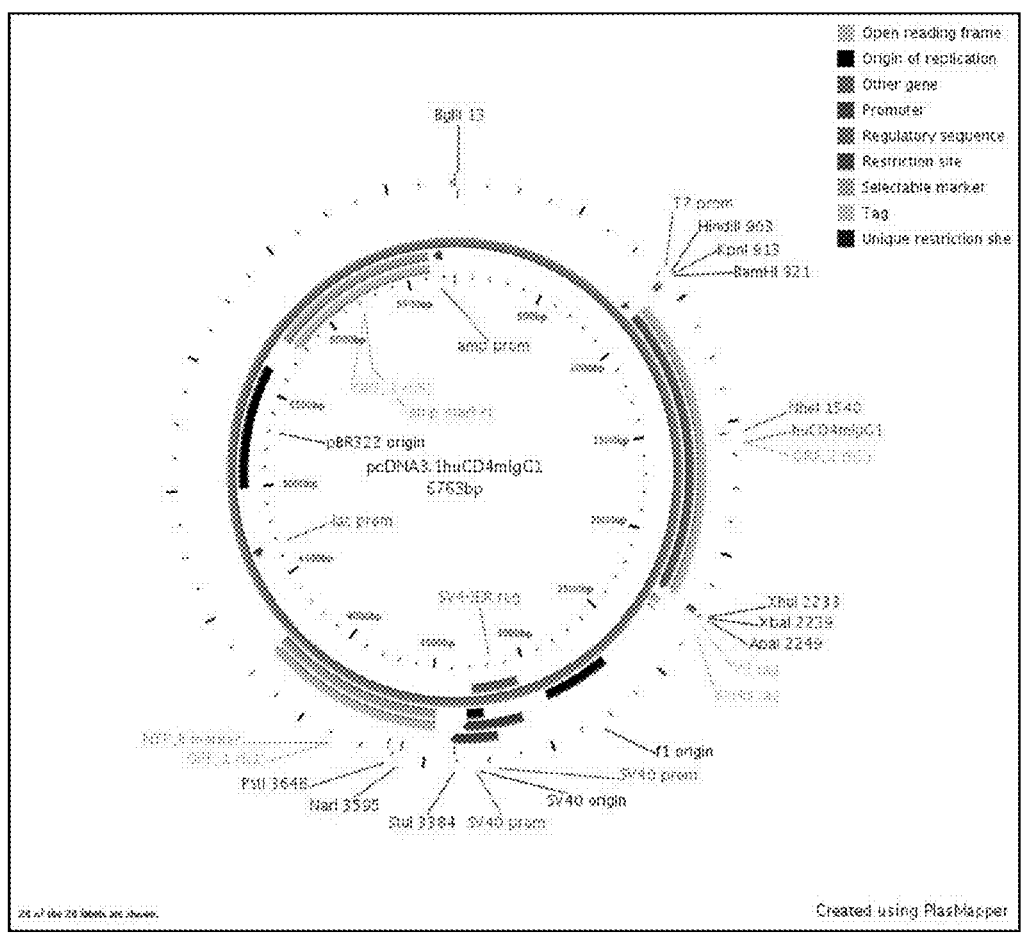
FIG. 1. Diagrams of the expression plasmid pcDNA3.1huCD4mIgG1. The main characteristics of the plasmid, such as selectable marker and open reading frame, are shown. The PlasMapper program (http://wishart.biology.ualberta.ca/PlasMapper/ August 2012) was used to draw the diagram.
Figure 1:
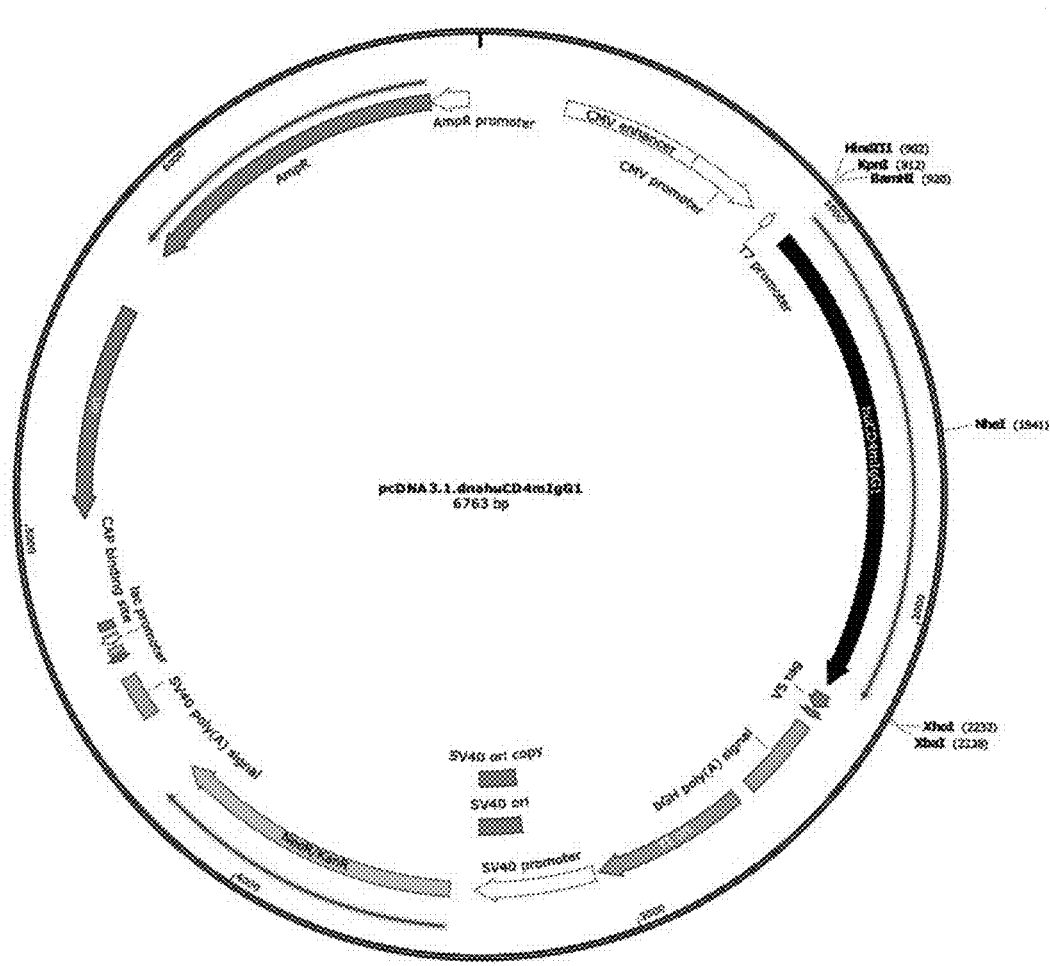

The plasmid pcDNA3.1huCD4mIgG1 was deposited on Jul. 25, 2012 at the DSMZ (Deutsche Sammlung von Mikroorganismen and Zellkulturen GmbH), Inhoffenstraβe 7 B, D-38124 Braunschweig, Federal Republic of Germany, under accession number DSM 26215.

DETAILED DESCRIPTION OF THE INVENTION

The present invention related to an assay for the identification and semi-quantification of HIV neutralizing antibodies in a sample. The test is based on the recognition of the Env glycoprotein on the surface of a HIV-infected cell by a huCD4/murine IgG1 fusion protein, although it can equally be carried out in different settings on which details are provided herein. An antibody will be considered as neutralizing if it is able to prevent the binding of the huCD4/IgG1 fusion protein to the gp120 on the surface of an infected cell. This novel approach offers several advantages: 1) HIV-infected cells express on their surface the Env glycoprotein with a functional and native conformation, 2) the use of a huCD4/murine IgG1 fusion protein mimics the natural interaction between gp120 and CD4, 3) the cytometric design makes this assay reproducible and low time-consuming, and 4) it is semi-quantitative and highly specific.

1. Definitions of General Terms and Expressions

The term "antibody producing cell", as used herein, refers to a cell capable of producing or secreting an antibody or a functional equivalent thereof, or which is capable of developing into a cell which is capable of producing or secreting an antibody or a functional equivalent thereof. An antibody producing cell according to the invention is preferably a producer cell which is adapted to commercial antibody production. More preferably, said producer cell is suitable for producing antibodies for use in humans.

The term "B cell", as used herein, refers to a type of lymphocyte that plays a large role in the humoral immune response (as opposed to the cell-mediated immune response, which is governed by T cells). The principal functions of B cells are to make antibodies against antigens, perform the role of antigen-presenting cells (APCs) and eventually develop into memory B cells after activation by antigen interaction. B cells are an essential component of the adaptive immune system.

The term "binding efficacy", as used herein, refers to the affinity of a compound, preferably an antibody, to the CD4 binding site of gp120. "Affinity" means the strength with which said compound binds to the CD4 binding site of gp120. It is determined by non-covalent interactions such as ionic interactions like attraction of opposite charges on amino acids, hydrogen bonds or hydrophobic interactions. As used herein, the term "binding" or "specifically binding", refers to the interaction between binding pairs (e.g. two proteins or compounds, preferably the CD4 binding domain of gp120 and CD4 or a compound, preferably an antibody, specific for this binding site). In some embodiments, the interaction has an affinity constant of at most $10^{-6}$ moles/liter, at most $10^{-7}$ moles/liter, or at most $10^{-8}$ moles/liter. In general, the phrase "binding" or "specifically binding" refers to the specific binding of one compound to another, wherein the level of binding, as measured by any standard assay, is statistically significantly higher than the background control for the assay.

The term "CD4", as used herein, refers to a cluster of differentiation 4, a glycoprotein expressed on the surface of T helper cells, monocytes, macrophages, and dendritic cells. CD4 is a co-receptor that assists the T cell receptor (TCR) with an antigen-presenting cell. Using its portion that resides inside the T cell, CD4 amplifies the signal generated by the TCR by recruiting an enzyme, known as the tyrosine kinase lck, which is essential for activating many molecules involved in the signaling cascade of an activated T cell. The complete protein sequence for human CD4 has the UniProt accession number P01730 (Jun. 18, 2012).

The term "codon optimized", as used herein, refers to the alteration of codons in nucleic acid molecules to reflect the typical codon usage of the host organism without altering the polypeptide encoded by the DNA, to improve expression. There are several methods and software tools known in the art for codon optimization. See Narum D, et al., Infect. Immun. 2001; 69(12):7250-7253), Outchkourov N, et al., Protein Expr. Purif. 2002; 24(1):18-24, Feng L, et al., Biochemistry 2000; 39(50):15399-15409, and Humphreys D, et al., Protein Expr. Purif. 2000; 20(2):252-264.

The term "comprising" or "comprises", as used herein, discloses also "consisting of" according to the generally accepted patent practice.

The term "FACS" or "fluorescent-activated cell sorting", as used herein, refers to a method for sorting a heterogeneous mixture of cells into one or more containers, one cell at a time, based upon the specific light scattering and fluorescent characteristics of each cell.

The term "fragment crystallizable region" or "Fc region", as used herein, refers to the tail region of an antibody that interacts with cell surface receptors called Fc receptors and some proteins of the complement system.

The term "fusion protein", as used herein, relates to proteins generated by gene technology which consist of two or more functional domains derived from different proteins. A fusion protein may be obtained by conventional means (e.g. by means of gene expression of the nucleotide sequence encoding for said fusion protein in a suitable cell).

The term "gp120", as used herein, refers to a glycoprotein having either the antigenic specificity or the biological function of the outer envelope protein (env) of HIV. A "gp120 protein" is a molecule derived from a gp120 region of an Env polypeptide. The mature gp120 wild-type polypeptides have about 500 amino acids in their primary sequence. Gp120 is heavily N-glycosylated giving rise to an apparent molecular weight of 120 kD. The amino acid sequence of gp120 is approximately 511 amino acids. Gp120 contains five relatively conserved domains (C1-C05) interspersed with five variable domains (V1-V5). The variable domains contain extensive amino acid substitutions, insertions and deletions. A "gp120 polypeptide" includes both single subunits and multimers. The gp41 portion is anchored in (and spans) the membrane bilayer of the virion, while the gp120 segment protrudes into the surrounding environment. The receptor binding domain of gp120 is localized to N-terminal half of the protein. This is followed by a proline rich region (PRR), which is proposed to behave either as a hinge or trigger to communicate receptor binding to the fusion machinery. The C-terminus of the gp120 is highly conserved and interacts with the gp41. Exemplary sequences of wt gp160 polypeptides are available. See GenBank accession nos. AAB05604 and AAD12142. Preferably, the gp120 polypeptide is derived from HIV Env.

Furthermore, a "gp120 polypeptide", as defined herein, is not limited to a polypeptide having the exact sequence described herein. Indeed, the HIV genome is in a state of constant flux and contains several variable domains that exhibit relatively high degrees of variability between isolates. It is readily apparent that the terms encompass gp120 polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g. isolates HIV IIIb, HIV SF2, HIV-1 SF162, HIV-1 SF170, HIV LAV, HIV LAI, HIV MN, HIV-1 CM235, HIV-1 US4, other HIV-1 strains from diverse subtypes (e.g. subtypes, A through G, and O), HIV-2 strains and diverse subtypes (e.g. HIV-2 UC1 and HIV-2 UC2), and simian immunodeficiency virus (SIV). See Joklik W, Ed., "Virology", $3^{rd}$ Ed. (Lippincott-Raven Publishers, Philadelphia, Pa., US, 1988), Fields B, et al., Eds., "Fundamental Virology", $3^{rd}$ Ed. (Raven Press, New York, N.Y., US, 1995), and Knipe D, et al., Eds., Fields Virology, $5^{th}$ Ed. (Lippincott Williams & Wilkins, New York, N.Y., US, 2006). Sequence comparison programs (e.g. BLAST and others described herein) or identification and alignment of structural features programs (e.g. "ALB" program for identifying β-sheet regions) may be used for comparing the sequence of the native and modified Env polypeptide sequences. The actual amino acid sequences of the modified Env polypeptides can be based on any HIV variant. Additionally, the term gp120 polypeptide) encompasses proteins that include additional modifications to the native sequence, such as additional internal deletions, additions and substitutions. These modifications may be deliberate, as through site-directed mutagenesis, or may be accidental, such as through naturally occurring mutational events.

The term "HIV", as used herein, refers to the human immunodeficiency virus. It includes HIV-1, HIV-2 and SIV; preferably, it relates to HIV-1 and/or HIV-2. "HIV-1" means the human immunodeficiency virus type-1. HIV-1 includes but is not limited to extracellular virus particles and the forms of HIV-1 associated with HIV-1 infected cells. The HIV-1 virus may represent any of the known major subtypes (Classes A, B, C, D E, F, G and H) or outlying subtype (Group O) including laboratory strains and primary isolates. "HIV-2" means the human immunodeficiency virus type-2. HIV-2 includes but is not limited to extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes but is not limited to extracellular virus particles and the forms of SIV associated with SIV infected cells.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Examples of algorithms suitable for determining sequence similarity include, but are not limited to, the BLAST, Gapped BLAST, and BLAST 2.0, WU-BLAST-2, ALIGN, and ALIGN-2 algorithms. See Altschul S, et al., Nuc. Acids Res. 1977; 25:3389-3402, Altschul S, et al., J. Mol. Biol. 1990; 215:403-410, Altschul S, et al., Meth. Enzymol. 1996; 266:460-480, Karlin S, et al., Proc. Natl. Acad. Sci. USA 1990; 87:2264-2268, Karlin S, et al., Proc. Natl. Acad. Sci. USA 1993; 90:5873-5877, Genentech Corp, South San Francisco, Calif., US, http://blast.ncbi.nlm.nih.gov/blast/, August 2012. Methods of alignment of sequences for comparison are well known in the art. Optimal alignment of sequences for comparison can be conducted, for instance, by the Smith-Waterman local homology algorithm, by the Needleman-Wunsch homology alignment algorithm, by the Pearson-Lipman similarity search method, by computerized implementations of these algorithms or by manual alignment and visual inspection. See Smith T, et al., Adv. Appl. Math. 1981; 2:482-489, Needleman S, et al., J. Mol. Biol. 1970; 48:443-453, Pearson W, et al., Lipman D, Proc. Natl. Acad. Sci. USA 1988; 85:2444-2448, the GAP, BESTFIT, FASTA and TFASTA programs, Wisconsin Genetics Software Package, Genetics Computer Group, Madison, Wis., USA; Ausubel F, et al., Eds, "Short Protocols in Molecular Biology", 5th Ed. (John Wiley and Sons, Inc., New York, N.Y., US, 2002).

The term "hybridoma", as used herein, refers to a cell that is created by fusing two cells, an antibody secreting cell from the immune system, such as a B-cell, and an immortal cell, such as a myeloma, within a single membrane.

The term "kit", as used herein, refers to a product containing the different reagents necessary for carrying out the methods of the invention packed so as to allow their transport and storage. Materials suitable for packing the components of the kit include crystal, plastic (e.g. polyethylene, polypropylene, polycarbonate), bottles, vials, paper, or envelopes. The kit of the invention can additionally contain instructions for using the components contained therein.

The term "known HIV neutralizing antibodies", as used herein, refers to HIV neutralizing antibodies known in the art. Preferably, a known HIV neutralizing antibody is selected from the group consisting of IgGb12, VRC01, VRC03, VRC-PG04, 3BNC60, HJ16, 3BNC117, NIH45-46, 8ANC131, and 12A12. See Waker L, et al., Nature 2011; 477(7365):466-470 and Scheid J, et al., Science 2011; 33(6049):1633-1637. Other HIV neutralizing antibodies include, but are not limited to, 2F5, 4E10, PG9, PG16, and 2G12.

The term "neutralizing antibody", as used herein, is any antibody or antigen-binding fragment thereof that binds to a pathogen and interferes with the ability of the pathogen to infect a cell or cause disease in a subject. Typically, the neutralizing antibodies used in the method of the present invention can bind to the surface of the pathogen and are able to inhibit or reduce infection by the pathogen by at least 99%, 95%, 90%, 85%, 80%, 75%, 70%, 60%, 50%, 45%, 40%, 35%, 30%, 25%, 20%, or 10% relative to the infection by the pathogen in the absence of said antibody(ies) or in the presence of a negative control. Methods for confirming whether an antibody is a nAb have been described in the art. See Li M, et al., J. Virol. 2005; 79:10108-10125, Wei X, et al., Nature 2003; 422:307-312, and Montefiori D, Curr. Protoc. Immunol. 2005; January, Chapter 12:Unit 12.11. These methods are based on the determination of the reduction in expression of a reporter gene after a single round of viral infection using a receptive cell line using a virus which encodes the reporter gene. In the context of the invention, this antigen is preferably gp120 and this infectious body is preferably HIV. In particular, the term "HIV neutralizing antibody" refers to an antibody with affinity to the CD4 binding site of gp120. The term "neutralizing antibodies" includes the subclass of bnAbs. As used herein, "broadly neutralizing antibody" or "bnAb" is understood as an antibody obtained by any method that when delivered at an effective dose can be used as a therapeutic agent for the prevention or treatment of HIV infection or AIDS against more than 7 strains of HIV, preferably more than 8, 9, 10, 11, 12, 13, 14, 15, 16, 17, 18, 19, 20, or more strains of HIV. The neutralizing capacity of the antibodies may be characterized by the IC50 (i.e. the concentration of antibody which causes a 50% reduction in the infection of a target cell). Preferably, neutralizing antibodies for use according to the present invention have an IC50 of 2 μg/ml or lower (less than 0.15 μg/mL, less than 0.125 μg/mL, less than 0.10 μg/mL, less than 0.075 μg/mL, less than 0.05 μg/mL, less than 0.025 μg/mL, less than 0.02 μg/mL, less than 0.015 μg/mL, less than 0.0125 μg/mL, less than 0.01 μg/mL, less than 0.0075 μg/mL, less than 0.005 μg/mL or less than 0.004 μg/mL (an antibody concentration of $10^{-8}$ or lower, preferably $10^{-9}$ M or lower, preferably $10^{-10}$ M or lower, i.e. $10^{-11}$ M, $10^{-12}$ M, $10^{-13}$ M or lower). This means that only very low concentrations of antibody are required for 50 percent neutralization of a clinical isolate of HIV in vitro. Potency can be measured using a standard neutralization assay as described in the art.

The term "operably linked", as used herein, means that the nucleotide sequence of interest is linked to the regulatory sequence(s) in a manner that allows for expression of the nucleotide sequence (e.g. in an in vitro transcription/translation system or in a host cell when the vector is introduced into the host cell). See Auer H, Nature Biotechnol. 2006; 24: 41-43.

The terms "polynucleotide" and "nucleic acid", as used herein, refer to a polymeric form of nucleotides of any length and formed by ribonucleotides or deoxyribonucleotides. The term includes both single and double stranded polynucleotides, as well as modified polynucleotides (e.g. methylated, protected and similar).

The terms "prevent," "preventing," and "prevention", as used herein, refer to inhibiting the inception or decreasing the occurrence of a disease in a subject. Prevention may be complete (e.g. the total absence of pathological cells in a subject) or partial. Prevention also refers to a reduced susceptibility to a clinical condition.

The terms "primary antibody" and "secondary antibody", as used herein, refer generally to two groups of antibodies based on whether they target a target of interest directly or target another (primary) antibody that, in turn, is bound to a target of interest. In the context of the present invention, the primary antibody does not target a target, as only its Fc region is used, which is fused to the protein capable of binding to the CD4 binding-site of gp120. The secondary antibody targets that Fc region.

The term "sample", as used herein, refers to any sample, preferably a biological sample, which may contain antibodies. For example, it can be the supernatant of a cell culture (e.g. a culture of B-cells, in particular a B-cell hybridoma). Also, it can be a sample collected from a subject. Suitable samples collected from a subject for use in the present invention include any biofluid and, in particular, blood, serum, plasma, lymph, saliva, peripheral blood cells or tissue cells serum, saliva, semen, sputum, cephalorachidian liquid (CRL), tears, mucus, sweat, milk, or brain extracts. The bodily tissue may comprise thymus, lymph node, spleen, bone marrow, or tonsil tissue. Preferred samples are plasma or serum. The term "control sample" refers to a sample which does not comprise any compound binding to the CD4 binding site of gp120.

The term "subject", as used herein, refers to an animal, in particular a vertebrate, such as a human, a non-human primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex. The term "subject" encompasses an embryo and a fetus.

The term "surface", as used herein, refers to the outer membrane of a cell, whereby "on its surface" can mean integrated into or attached to the surface or membrane. In any case the CD4 binding site of gp120 is outside of the cell and exposed such that binding can occur.

The term "treat" or "treatment", as used herein, refers to the administration of a compound of the invention or of a composition or medicament containing it to control the progression of a disease after its clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state and remission (both partial and total). The control of progression of the disease also involves an extension of survival, compared with the expected survival if treatment was not applied.

The term "vector", as used herein, refers to a nucleic acid molecule, linear or circular, that comprises a segment according to the nucleic acid of interest operably linked to additional segments that provide for its autonomous replication in a host cell of interest or according to the expression cassette of interest.

2. Method for Determining HIV Neutralizing Antibodies in a Sample

In a first aspect, the invention relates to an in vitro method for determining HIV neutralizing antibodies in a sample, comprising:
  a) contacting a cell comprising the CD4 binding site of gp120 on its surface with said sample and with a fusion protein comprising (i) a protein capable of binding to the CD4 binding-site of gp120 and (ii) a Fc region of a primary antibody, and
  b) measuring the binding efficacy of said fusion protein to the CD4 binding site of gp120,
wherein HIV neutralizing antibodies are determined in said sample if said binding efficacy is lower than the binding efficacy determined in the absence of any neutralizing antibodies.

In a first step, the method for determining HIV neutralizing antibodies in a sample comprises contacting a cell comprising the CD4 binding site of gp120 on its surface with said sample and with a fusion protein comprising (i) a protein capable of binding to the CD4 binding-site of gp120 and (ii) a Fc region of a primary antibody.

In a preferred embodiment, the sample can be a supernatant of a cell culture, e.g. a culture of B-cells, in particular a B-cell hybridoma. Also, it can be a sample collected from a subject. In a more preferred embodiment, the sample is a plasma sample or a serum sample.

The contacting is carried out by at least an instance of exposure of said cell, said sample and said fusion protein. In a preferred embodiment, the exposure is prolonged (i.e. an incubation under conditions suitable for the cell to survive and for specific binding of the CD4 binding site of gp120 and the fusion protein of the invention). The conditions during the contacting step can be determined in a routine manner by the skilled artisan. Suitable buffers that can be used in the contacting step include physiological buffers that do not interfere with the assay to be performed. For example, a Tris or a Triethanolamine (TEA) buffer can be employed. The pH of the buffer (and resulting lysis reagent including the buffer solution) can range from about 2.0 to about 10.0, optionally from about 4.0 to about 9.0, preferably from about 7.0 to about 8.5, even more preferably from about 7.5 to about 8.0, or, about 7.0, about 7.5, about 8.0, or about 8.5. Exemplary "contacting" conditions may comprise incubation for 15 minutes to 4 hours (e.g. one hour, at 4° C., 37° C. or at room temperature). However, these may be varied as appropriate according to, for example, the nature of the interacting binding partners. The sample may optionally be subjected to gentle rocking, mixing or rotation. In addition, other appropriate reagents such as blocking agents to reduce non specific binding may be added. For example, 1-4 percent BSA or other suitable blocking agent (e.g. milk) may be used. The contacting conditions can be varied and adapted depending on the aim of the screening method. For example, if the incubation temperature is, for example, room temperature or 37° C., this may increase the possibility of identifying binders which are stable under these conditions (e.g. in the case of incubation at 37° C., binders which are stable under conditions found in the human body). Such a property might be extremely advantageous if one or both of the binding partners was a candidate to be used in some sort of therapeutic application (e.g. an antibody).

The cell to be used can be of any type, including both eukaryotic cells and prokaryotic cells. Preferably, the cell is a cultivated eukaryotic, more preferably a cultivated mammalian cell (e.g. a cultivated human cell). Preferred examples of mammalian cells are, for instance, HEK-293 cells, MOLT-3 cells, COS cells, HeLa cells, 293T cells and cells of any other established cell lines. In addition, cells should preferably be able to express the fusion protein of the invention in a functional and conformational native state. In one embodiment, said cell is a HIV-infected cell. Preferably, said HIV-infected cell is chronically infected. In one specific embodiment, said chronically HIV-infected cell is selected from the group consisting of a NL4.3 chronically infected MOLT cell, a H9 cell, and a HuT-78 cell. See Blanco J, et al., Leukoc. Biol. 2004; 76(4):804-811 and Blanco J, et al., Virology 2003; 305(2):318-329.

The order in which the different components of the assay are contacted is not particularly limiting. Thus, in one embodiment, the cells expressing CD4 binding site of gp120 on its surface are contacted first with the fusion protein and later on with the sample. In another embodiment, the cells expressing CD4 binding site of gp120 on its surface are contacted first with the sample and then with the fusion protein. In yet another embodiment, the fusion protein and the sample are mixed and the mixture is then added to the cells expressing CD4 binding site of gp120 on its surface. In another embodiment, the fusion protein, the sample and the cells expressing CD4 binding site of gp120 on its surface are contacted at the same time.

The "CD4 binding site of gp120" is determined by sequence and conformation of gp120. Although the main region of gp120 involved in the binding to CD4 is the CD4 binding-loop 364-SSGGDPEIVTH-374 (HXB2 numbering PO4578), the conformational CD4bs in gp120 involves other residues from the fourth constant region of this protein. In particular, D368 (HXB2 numbering) is a key residue, since its mutation abrogates CD4 binding. The characterization of CD4bs has been published previously. See Sterjovski J, et al., Virology 2011; 410(2):418-428. It is preferred that the CD4 binding site of gp120 has a functional and native conformation. One way of providing such a CD4 binding site is using the gp120 protein, the Env protein or fragments thereof comprising said binding site.

In a preferred embodiment, the protein capable of binding to the CD4 binding-site of gp120 is preferably selected from CD4 or a functionally equivalent variant thereof. In a preferred embodiment, the protein capable of binding to the CD4 binding-site of gp120 is CD4. Said CD4 is preferably derived from an animal, in particular a vertebrate, such as a human (e.g. UniProtKB database accession number P01730), a non-human primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. In another preferred embodiment, the protein capable of binding to the CD4 binding-site of gp120 is a functionally equivalent variant of CD4.

Variants of CD4 may be both natural and artificial. The expression "natural variant" relates to all those variants of human CD4 mentioned above which appear naturally in other species (i.e. CD4 orthologs). Said natural variants include, without limitation, CD4 mouse or chicken orthologs (NCBI database accession numbers NP_038516.1 and NP_989980.1, respectively). The natural variants of CD4 suitable for their use in the present invention may also derive from said sequences by insertion, substitution or deletion of one or more amino acids and include natural alleles, variants resulting from alternative processing and secreted and truncated forms which appear naturally.

A functionally equivalent variant of CD4, as used in the present invention, refers to a polypeptide resulting from the modification, deletion or insertion or one or more amino acids and which substantially preserves the activity of CD4. Assays adequate to determine whether a polypeptide can be seen as a functionally equivalent variant of CD4 include the assay shown in example 3 of the present invention, based on the ability of the polypeptide to bind to a cell expressing gp120 in its surface. The assay can be carried out by contacting a cell expressing gp120 with a fusion protein comprising an antibody Fc fragment and the suspected variant. A polypeptide can be seen as a functionally equivalent variant of CD4 if it shows at least 100%, 95%, 90%, 85%, 80%, 75%, 70%, 65%, 60%, or less of the binding efficacy of the human CD4 mentioned above.

Functionally equivalent variants of CD4 contemplated in the context of the present invention, include polypeptides which show at least 60%, 70%, 80%, 85%, 90%, 92%, 94%, 96%, 98%, 99% of similarity or identity with the different natural variants of CD4 mentioned above. The percentage of identity between two sequences indicates the proportion of identical amino acids that share the two sequences that are compared, whilst the percentage of similarity indicates the proportion of residues of similar amino acids (considering equivalent the residues of amino acids such as arginine and lysine or aspartic acid and glutamic acid). The percentage of identity between two sequences of amino acids is calculated by comparing two sequences aligned on a particular region, determining the number of positions wherein there are identical amino acids in both sequences to obtain the number of coincident positions by dividing the number of said positions by the number of total positions in the segment which is being compared and multiplying the result by 100. The degree of identity and similarity between two polypeptides is determined using computer-implemented algorithms and methods that are widely known in the art. The identity and similarity between two sequences of amino acids is preferably determined using the BLASTP algorithm. See Altschul S, et al., "BLAST Manual" (NCBI NLM NIH, Bethesda, Md., US, 2001).

In another embodiment, the functionally equivalent variant of CD4 is a fragment of CD4 comprising at least the D1-D2 N-terminal domains of CD4. The D1 domain of CD4 (also known as Ig-like V-type) comprises amino acids 26-125 of CD4 according to the numbering of the human CD4 (i.e. UniProtKB database accession number P01730). The D2 domain of CD4 (also known as Ig-like C2-type 1) comprises amino acids 126-203 of CD4 according to the numbering of the human CD4. In different embodiment, a larger fragment of CD4 (D1-D4) is used. See, et al., J. Virol. 2011; 85(18):9395-9405. The D2 domain of CD4 includes a NheI restriction site. The site is located at the C-terminal (603-608 bp). In another embodiment, a variant of the CD4-fragment is used instead having at least 80%, 85%, 90%, 95%, or 99% similarity to CD4-fragment, wherein said variant can bind to the CD binding site of gp120. Preferably, the CD4-fragment has comprises a sequence of SEQ ID NO: 8.

In one embodiment, said primary antibody is selected from the group consisting of IgA (e.g. IgA1 or IgA2), IgD, IgE, IgG (e.g. IgG1, IgG2, IgG3 or IgG4), and IgM and preferably is IgG, more preferably IgG1. It is preferred that said primary antibody is from a different species than the species said biological sample is derived from. Said primary antibody can be any vertebrate antibody, preferably any mammal antibody, and more preferably, any non-human antibody (e.g. a rabbit, mouse, rat, goat, horse, sheep or donkey antibody). In one embodiment, said primary antibody is murine IgG, preferably murine IgG1.

In another embodiment, a variant of the Fc region is used instead having at least 80%, 85%, 90%, 95%, or 99% similarity to Fc region, wherein said variant can bind to the corresponding secondary antibody of said Fc region. Preferably, the Fc region has the sequence of SEQ ID NO: 9.

In a most preferred embodiment, said fusion protein capable of binding to the CD4 binding-site of gp120 comprises or consists of the D1-D2 N-terminal domains of human CD4 and said (ii) Fc region of a primary antibody is the Fc region of murine IgG1. In a more preferred embodiment, said fusion protein has the amino acid sequence according to SEQ ID NO: 7 or a variant at least 80%, 85%, 90%, 95%, or 99% identical thereto, wherein preferably said variant can bind to a corresponding secondary antibody of said Fc region. "Corresponding secondary antibody of said Fc region" means that the Fab fragment of the secondary antibody binds to the Fc region of the primary antibody (i.e. is specific for the species of the primary antibody). In another embodiment, the fusion protein capable of binding to the CD4 binding-site of gp120 is encoded by the polynucleotide according to SEQ ID NO:10.

Said fusion protein may also contain a linker linking (i) said protein capable of binding to the CD4 binding-site of gp120 and (ii) said Fc region of a primary antibody. Such a linker can facilitate enhanced flexibility of the fusion protein, and it can also reduce steric hindrance between the two fragments, and allow appropriate binding interactions. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the λcI and LexA proteins. Alternatively, the linker can be of synthetic origin. For instance, the sequence $(Gly_4Ser)_3$ can be used as a synthetic unstructured linker. See Huston J, et al., Proc. Natl. Acad. Sci. USA 1988; 85:4879-4887 and Huston J, et al., U.S. Pat. No. 5,091,513. Another exemplary embodiment includes a poly alanine sequence (e.g. $(Ala)_3$).

In another embodiment, the fusion protein is a disulfide-linked homodimer.

In a second step, the method for determining HIV neutralizing antibodies according to the invention comprises measuring the binding efficacy of said fusion protein to the CD4 binding site of gp120.

Preferably, said HIV neutralizing antibodies can bind to the surface of the cell comprising the CD4 binding site of gp120 and reduce the binding of the fusion protein of the invention, preferably by at least 99%, 95%, 90%, 85%, 80%, 75%, 70%, 60%, 50%, 45%, 40%, 35%, 30%, 25%, 20%, or 10% compared to a negative control. More preferably, said HIV neutralizing antibodies are antibodies which have an affinity to the CD4 binding site of gp120 that is at least as high as that of CD4.

Appropriate binding studies depend on the nature of the binding partners, and include, but are not limited to, immunoassays (e.g. ELISA), filter screening assays, FACS, or immunofluorescence assays, or other methods to quantify binding constants, staining tissue slides or cells and other immunohistochemical methods. Such methods are well known in the art and may be used to measure said binding efficacy.

Preferably, said measuring is performed by flow cytometry (e.g. FACS). As used herein, the term "flow cytometry" refers to an assay in which the proportion of a material in a sample is determined by labeling the material (e.g. by binding a labeled antibody to the material), causing a fluid stream containing the material to pass through a beam of light, separating the light emitted from the sample into constituent wavelengths by a series of filters and mirrors, and detecting the light. Flow cytometry permits sensitive detection and rapid quantification of some features of single cells, such as relative size complexity, and endogenous fluorescence, as well as the quantitative analysis of any cellular compound that can be labeled with a fluorochrome. See Melamed M, et al., "Flow Cytometry and Cell Sorting", $2^{nd}$ Ed. (Wiley-Liss, New York, N.Y., US, 1990). One of the main advantages of flow cytometry is the rapid quantification of analytes on a large number of particles or cells. Generally, the fluorochromes selected for use as detectable markers are selected based on the ability of the fluorochrome to fluoresce when excited by light with the wavelength used by the laser. When the fluorochrome is excited by the laser beam, it emits light which is then assessed by the photomultiplier tubes of the flow cytometer. This technique is capable of analyzing 10,000 cells/particles within 1 to 2 minutes. Flow cytometers have filters to detect the emittance from various fluorochromes which fluoresce at different wavelengths, and allow for four or more different fluorochromes to be used as detectable markers which means currently at least 4 different molecules may be detected simultaneously. These methods and apparatus for analyzing cells are commercially available and are well known in the art (e.g. FACSCalibur Flow Cytometer; BD Biosciences Corp., Franklin Lakes, N.J., US).

In one embodiment, said measuring comprises the detection of fusion protein bound to said cell using a reporter capable of binding to said fusion protein, preferably to the Fc region of said fusion protein.

In a preferred embodiment, said measuring comprises analyzing said cell, preferably by flow cytometry, using a reporter capable of binding to said fusion protein, preferably to the Fc region of said fusion protein. Said reporter preferably comprises a detectable moiety and, more preferably, is a Fc-specific secondary antibody coupled to a detectable moiety.

Useful detectable moieties include fluorophores. By "fluorophore" (or "fluorochrome" or "chromophore") is a fluorescent compound that can re-emit light upon light excitation. Fluorophores that can be used include biological (e.g. proteins) and chemical fluorophores. Exemplary biological fluorophores comprise T-sapphire, Cerulean, mCFPm, CyPet, EGFP, PA-EGFP, Emerald, EYFP, Venus, mCitrine, mKO, mOrange, DSRed, JRed, mStrawberry, mCherry, PA-mCherry, mRuby, Tomato, mPlum, mKate, mKatushka, Kaede, Halotag, and superecliptic fluorine. Exemplary chemical fluorophores comprise Alexafluor, Rhodamine, BODIPY, Tetramethylrhodamine, Cyanin dyes, Fluorescein, Quantum dots, IR dyes, FM dyes, ATTO dye. A secondary antibody can also be labeled with enzymes that are useful for detection, such as, for example, horseradish peroxidase, β-galactosidase, luciferase, alkaline phosphatase, or glucose oxidase. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

Preferably, said Fc-specific secondary antibody is specific for the species said primary antibody is derived from. In one embodiment, said Fc-specific secondary antibody is selected from the group consisting of IgA (e.g. IgA1, IgA2), IgD, IgE, IgG (e.g. IgG1, IgG2, IgG3, IgG4), and IgM. Preferably, the secondary antibody is IgG. Said Fc-specific secondary antibody can be any vertebrate antibody, preferably any mammal antibody, and more preferably any non-human antibody (e.g. a rabbit, mouse, rat, goat, horse, sheep or donkey antibody).

In another embodiment of the method of the first aspect, step (i) is preceded by one or more washing steps removing unbound fusion protein. The washing steps may be carried out in any appropriate way depending on the cell and the binding partners of the CD4 binding site of gp120. The cell may be washed with any suitable medium, e.g. a cell culture medium or a buffer such as PBS. The medium may contain a detergent such as Tween20. It may be washed for any suitable time, e.g. 1 to 30 minutes or 3 to 10 minutes for each wash. Washing may include gentle shaking or rocking of the carrier of said cell. The washing temperature is such that the cell can survive and binding is not disrupted. For example, it can be between 20 and 45° C. or between 30 and 40° C. Typically, it is about 37° C. or room temperature. The protocols for washing the fusion protein are well known in the art.

Once the binding efficacy of the fusion protein to the cell comprising the CD4 binding site of gp120 on its surface is determined, the method of the invention comprising determining HIV neutralizing antibodies in the sample if said binding is inhibited in the presence of the sample.

An inhibition of the binding refers to a binding which is at least 5%, 10%, 20%, 30%, 40%, 50%, 60%, 70%, 80%, 90%, or 100% with respect to the binding in the presence of a control sample.

In a preferred embodiment, an inhibition of the binding is determined by assessing the binding efficacy in the sample in the presence of the fusion protein mentioned above and in a parallel reaction in the absence of the fusion protein and in the absence of any compound capable of binding to the CD4 binding site of gp120. In this situation, the sample is determined as containing nAb if the binding of the fusion protein to the cell is lower when compared to the binding of the fusion protein to the cell in the presence of a sample which does not contain any other compound capable of binding to the CD4 binding site of gp120. Suitable samples that can be used for carrying the method of the invention include samples of the same nature than the sample under study and which is known not to contain any nAb. In one embodiment, when the sample being analyzed is a sample from a patient, the control sample can be a sample of the same nature from a patient which has no known history of HIV infection or which has been infected with HIV but has not developed nAb. In another embodiment, when the sample being analyzed is a tissue culture supernatant, the control sample can be a culture supernatant from cells which are known not to produce any nAb or from ells which express Ab which have no affinity towards gp120.

The method of the first aspect can be used to determine the presence or absence of an HIV neutralizing antibody in a sample. To this end, a value is taken as a reference. The term "reference value" is a threshold value used to determine if neutralizing antibodies are present or not. If the amount of neutralizing antibodies determined in a sample exceeds the reference amount, neutralizing antibodies are present; if the amount of neutralizing antibodies determined in a sample is equal or lower than the reference value, neutralizing antibodies are absent. Likewise, if binding of the fusion protein to the cell exceeds the reference amount, neutralizing antibodies are absent; if binding of the fusion protein to the cell is equal or lower than the reference amount, neutralizing antibodies are present. The reference value can be established by, for example, quantifying the amount of neutralizing antibodies in a representative set of samples from subjects neither infected with nor immunized against HIV and analyzing statistically the results obtained to determine the reference amount. It is to be understood that the reference amount can, preferably, be zero or below the detectable limit of the assay used for determining the reporter gene activity. Thus, the reference amount can be obtained, preferably, from a cell as defined above which has been contacted to a sample known not to comprise neutralizing antibodies.

The method of the first aspect can be used to determine the presence of an HIV neutralizing antibody, but also to quantify an HIV neutralizing antibody. Accordingly, the invention also relates to the method of the first aspect, wherein said determination is a quantitative determination. The term "quantitative determination" comprises a semi-quantitative determination (i.e. an approximation of the quantity). Therein, it is preferred that in the method of the first aspect, said at least one control is a positive control. Preferably, at least 2, 3, 5, 10, 15, or 20 positive controls are used, each comprising a unique amount of compound binding to the CD4 binding site of gp120. In other words, a positive control is used as a standard in different concentrations of the compound binding to the CD4 binding site of gp120. The binding efficacy values obtained can be used to draw a standard curve which can then be used to derive the quantity of the HIV neutralizing antibody to be determined quantitatively.

Preferably, determining the presence of neutralizing antibodies referred to in this invention relates to determining the presence of said antibodies or to measuring their amount or concentration, preferably semi-quantitatively or quantitatively. Most preferably, the amount is measured as a titer (i.e. the maximum dilution of a sample that still affects a predetermined degree of binding efficacy). Preferably, the determination includes a normalization step for the quantification of neutralizing antibodies. Normalization and thus quantification is preferably achieved by adding a predefined amount of characterized neutralizing antibodies to a reaction mixture. Preferably, said characterized neutralizing antibodies are antibodies where the amount required for attaining a certain level of neutralization has been pre-determined. The principle of the normalization is to determine the amount or dilution of sample required to achieve the same level of neutralization (e.g. 50% inhibition of binding as compared to the inhibition by a pre-defined amount of characterized neutralizing antibodies). For quantification, neutralization can be compared to a standard curve using characterized neutralizing antibodies or to other suitable reference material following protocols well known in the art. The quantitative method can include the above-mentioned binding studies, such as, for example, immunoassays (e.g. ELISA), filter screening assays, FACS, or immunofluorescence assays, or other methods to quantify binding constants, staining tissue slides or cells and other immunohistochemical methods.

3. Fusion Protein and Nucleic Acid of the Invention

In another aspect, the present invention relates to a fusion protein comprising (i) a protein capable of binding to the CD4 binding-site of gp120 and (ii) a Fc region of a primary antibody.

In a preferred embodiment, the protein capable of binding to the CD4 binding-site of gp120 is CD4 or a functionally equivalent variant thereof. In a more preferred embodiment, the functionally equivalent variant of CD4 is a fragment of CD4 comprising at least the D1-D2 N-terminal domains of CD4.

In another embodiment, the Fc region derives from a primary antibody selected from the group consisting of IgA (e.g. IgA1 or IgA2), IgD, IgE, IgG (e.g. IgG1, IgG2, IgG3 or IgG4), and IgM. Preferably, the antibody is IgG. More preferably, it is IgG1. Said primary antibody can be any vertebrate antibody, preferably any mammal antibody, and more preferably any non-human antibody (e.g. a rabbit, mouse, rat, goat, horse, sheep or donkey antibody). In one embodiment, said primary antibody is murine IgG, preferably murine IgG1.

Said fusion protein may also contain a linker linking (i) said protein capable of binding to the CD4 binding-site of gp120 and (ii) said Fc region of a primary antibody. Such a linker can facilitate enhanced flexibility of the fusion protein, and it can also reduce steric hindrance between the two fragments, and allow appropriate binding interactions. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase α subunit. Other examples of naturally occurring linkers include linkers found in the λcI and LexA proteins. Alternatively, the linker can be of synthetic origin. For instance, the sequence $(Gly_4Ser)_3$ can be used as a synthetic unstructured linker. See Huston, 1988, supra. Another exemplary embodiment includes a poly alanine sequence (e.g. $(Ala)_3$).

In another aspect, the invention relates to a nucleic acid encoding the fusion protein of the second aspect and to an expression cassette, or a vector comprising said nucleic acid.

Preferably, said nucleic acid is a polynucleotide, referring to single-stranded or double-stranded polymers of nucleotide monomers (nucleic acids), including, but not limited to, 2'-deoxyribonucleotides (DNA) and ribonucleotides (RNA) linked by internucleotide phosphodiester bond linkages.

Alternatively, the polynucleotides encoding a functionally equivalent variant of CD4 include polynucleotides capable of coding for a variant of the polypeptides with CD4 activity, as defined above by their specific sequences. Said polynucleotides result from previously defined polynucleotides by means of the insertion, deletion or substitution of one or several nucleotides with respect to the aforementioned sequences. Preferably, the polynucleotides which code for functionally equivalent variants of CD4 are polynucleotides whose sequence allows them to hybridize in highly restrictive conditions with the aforementioned polynucleotides. Typical conditions of highly restrictive hybridization include incubation in 6×SSC (1×SSC: 0.15 M NaCl, 0.015 M sodium citrate) and 40% formamide at 42° C. during 14 hours, followed by one or several washing cycles using 0.5×SSC, 0.1% SDS at 60° C. Alternatively, highly restrictive conditions include those comprising a hybridization at a temperature of approximately 50°-55° C. in 6×SSC and a final washing at a temperature of 68° C. in 1-3×SSC. Moderate restrictive conditions comprise hybridization at a temperature of approximately 50° C. until around 65° C. in 0.2 or 0.3 M NaCl, followed by washing at approximately 50° C. until around 55° C. in 0.2×SSC, 0.1% SDS (sodium dodecyl sulphate). In one further embodiment, said nucleic acid is codon optimized.

In another embodiment, a variant of the nucleic acid is used instead having at least 80%, 85%, 90%, 95%, or 99% similarity to the nucleic acid, wherein said variant encodes the fusion protein of the invention.

The nucleic acid of the second aspect may require to be cut with restriction enzymes in order to be ligated into a vector (i.e. some terminal nucleotides may be removed, e.g. 1, 2, or 3). As such, in one embodiment, the invention relates to said nucleic acid, wherein it has been cut at each end with a restriction enzyme.

In another embodiment, the present invention relates to an expression cassette comprising the nucleic acid of the second aspect, a promoter sequence and a 3'-UTR and optionally a selection marker. In yet another embodiment, the present invention relates to an expression vector comprising the nucleic acid or the expression cassette of the second aspect. Suitable vectors according to the present invention include prokaryotic vectors, such as pUC18, pUC19, and Bluescript plasmids and derivatives thereof, like the mp18, mp19, pBR322, pMB9, ColE1, pCR1 and RP4 plasmids; phages and shuttle vectors, such as pSA3 and pAT28 vectors; expression vectors in yeasts, such as 2-micron plasmid type vectors; integration plasmids; YEP vectors; centromeric plasmids and analogues; expression vectors in insect cells, such as the vectors of the pAC series and of the pVL series; expression vectors in plants, such as vectors of the pIBI, pEarleyGate, pAVA, pCAMBIA, pGSA, pGWB, pMDC, pMY, pORE series and analogues; and expression vectors in superior eukaryotic cells either based on viral vectors (e.g. adenoviruses, viruses associated to adenoviruses, retroviruses and lentiviruses) as well as non-viral vectors, such as the pSilencer 4.1-CMV (Ambion®, Life Technologies Corp., Carlsbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d, and pTDT1 vectors. In one embodiment, the vector is an expression vector.

In another embodiment, the present invention relates to a transgenic cell comprising the nucleic acid, the expression cassette, or the expression vector of the second aspect. Transgenic tells to be used can be of any cell type, including both eukaryotic cells and prokaryotic cells. Preferably, the cells include prokaryotic cells, yeast cells, or mammalian cells.

4. Kits of the Invention

In another aspect, the invention relates to a kit comprising the (i) fusion protein of the second aspect, the nucleic acid, the vector or the transgenic cell of the third aspect and (ii) a reporter capable of binding to said fusion protein. In one embodiment, said kit may further comprise at least one cell comprising the CD4 binding site of gp120 on its surface. Said cell is a cell as defined in the method of the first aspect.

5. Method for the Identification of B-Cells Expressing HIV Neutralizing Antibodies The assay of the present invention can also be used to detect antibody-producing cells which are capable of expressing neutralizing antibodies by applying the assay to a supernatant of a culture of the antibody-expressing cells. Thus, in another aspect, the invention relates to an in vitro method for the identification of antibody-producing cells expressing HIV neutralizing antibodies, comprising:
  (i) contacting a cell comprising the CD4 binding site of gp120 on its surface with a supernatant of a culture of said antibody-producing cells and with a fusion protein comprising (i) a protein capable of binding to the CD4 binding-site of gp120 and (ii) a Fc region of a primary antibody, and
  (ii) measuring the binding efficacy of said fusion protein to the CD4 binding site of gp120
wherein the antibody-producing cells are determined as expressing HIV neutralizing antibodies if said binding efficacy is different from that of at least one control.

In a first step, a cell comprising the CD4 binding site of gp120 on its surface is contacted with a supernatant of a culture of said antibody-producing cells and with a fusion protein comprising (i) a protein capable of binding to the CD4 binding-site of gp120 and (ii) a Fc region of a primary antibody. The conditions for the contacting step are essentially as described above for the contacting of a sample. In a preferred embodiment, the antibody-producing cells are B cells, which are usually non-immortal. In another embodiment, the antibody-producing cells are hybridoma cells, which are usually immortal.

In a preferred embodiment, the protein capable of binding to the CD4 binding-site of gp120 is preferably selected from CD4 or a functionally equivalent variant thereof. In a still more preferred embodiment, the functionally equivalent of CD4 is a CD4-fragment comprising at least the D1-D2 N-terminal domains of CD4. In one embodiment, the CD4 is preferably derived from an animal, in particular a vertebrate, such as a human, a non-human primate (e.g. chimpanzees and other apes and monkey species), farm animals (birds, fish, cattle, sheep, pigs, goats and horses), domestic mammals (e.g. dogs and cats), and laboratory animals (e.g. rodents, such as mice, rats and guinea pigs). In another embodiment, the Fc region of a primary antibody is the Fc region of murine IgG1.

The order in which the different components of the assay are contacted is not particularly limiting. Thus, in one embodiment, the cells expressing CD4 binding site of gp120 on its surface are contacted first with the fusion protein and later on with the culture supernatant. In another embodiment, the cells expressing CD4 binding site of gp120 on its surface are contacted first with the culture supernatant and then with the fusion protein. In yet another embodiment, the fusion protein and the culture supernatant are mixed and the mixture is then added to the cells expressing CD4 binding site of gp120 on its surface. In another embodiment, the fusion protein, the culture supernatant and the cells expressing CD4 binding site of gp120 on its surface are contacted at the same time.

In a second step, the binding efficacy of the fusion protein to the CD4 binding site of gp120 in the cell is determined. Suitable methods for determining binding of the fusion protein to the cell expressing gp120 have been described in detail above in the context of the method for determining HIV neutralizing antibodies in a sample. In one embodiment, said measuring comprises the detection of fusion protein bound to said cell using a reporter capable of binding to said fusion protein, preferably to the Fc region of said fusion protein. In a preferred embodiment, said measuring comprises analyzing said cell, preferably by flow cytometry, using a reporter capable of binding to said fusion protein, preferably to the Fc region of said fusion protein. Said reporter preferably comprises a detectable moiety and, more preferably, is a Fc-specific secondary antibody coupled to a detectable moiety.

Once the binding efficacy of the fusion protein to the cell comprising the CD4 binding site of gp120 on its surface is determined, the method of the invention comprising determining the antibody-producing cell as producing HIV neutralizing antibodies if said binding is inhibited in the presence of the sample. An inhibition of the binding refers to a binding which is at least 5%, 10%, 20%, 30%, 40%, 50%, 60%, 70%, 80%, 90%, or 100% with respect to the binding in the presence of a control sample.

If the antibody-producing cells are a non-homogenous population, the cells can be cloned and further selected based on the production of neutralizing antibodies in order to obtain an homogenous cell population. Clones may be subcloned by limiting dilution procedures and grown by standard methods. See Goding J, "Monoclonal Antibodies: Principles and Practice", 3rd Ed. (Academic Press, Waltham, Mass., US, 1996). Suitable culture media for this purpose include, for example, D-MEM or RPMI-1640 medium. If the antibody-producing cells are hybridoma cells, the cells may be grown in vivo as ascites tumor cells in an animal.

6. Methods for Obtaining Neutralizing Antibodies

In another aspect, the invention refers a method for producing HIV neutralizing antibodies which comprises:

a) culturing an hybridoma comprising a B-cell isolated according to method for the isolation of B cells expressing neutralizing antibodies and
b) isolating the HIV neutralizing antibodies expressed by said hybridoma.

The antibody producing cells expressing neutralizing antibodies, once selected according to the methods defined above, are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The antibodies can be isolated from the cells or may be obtained by recombinant means by expressing the relevant regions of the immunoglobulin genes of the cells which are responsible for antigen specificity in suitable cells.

Antibodies can be purified from the culture supernatant of antibody-producing cells by methods known in the art such as anion/cation exchange, size-exclusion/gel filtration, precipitations and the use of specific affinity ligands. Commonly used affinity ligands are bacterially derived Protein-A and Protein-G, monoclonal antibodies and camelid antibodies or binding fragments derived therefrom that bind one or more of the four subclasses of human or humanized IgG.

In the case that the antibodies are produced by recombinant means, the polynuceotides encoding the relevant regions of the immunoglobulin molecule are isolated. One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest (e.g. variable region peptides with desired binding characteristics) can be identified by standard techniques known in the art (e.g. panning).

Relevant amino acid sequences from an immunoglobulin or polypeptide of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g. by using oligonucleotide probes that are capable of binding specifically to genes encoding the heavy and light chains of the monoclonal antibodies). See Brown T, "Gene Cloning" (Chapman & Hall, London, GB, 1995); Watson R, et al., "Recombinant DNA", 2nd Ed. (Scientific American Books, New York, N.Y., US, 1992); Alberts B, et al., "Molecular Biology of the Cell" (Garland Publishing Inc., New York, N.Y., US, 2008); Innis M, et al., Eds., "PCR Protocols. A Guide to Methods and Applications" (Academic Press Inc., San Diego, Calif., US, 1990); Erlich H, Ed., "PCR Technology. Principles and Applications for DNA Amplification" (Stockton Press, New York, N.Y., US, 1989); Sambrook J, et al., "Molecular Cloning. A Laboratory Manual" (Cold Spring Harbor Laboratory Press, Cold Spring Harbor, N.Y., US, 1989); Bishop T, et al., "Nucleic Acid and Protein Sequence. A Practical Approach" (IRL Press, Oxford, GB, 1987); Reznikoff W, Ed., "Maximizing Gene Expression" (Butterworths Publishers, Stoneham, Mass., US, 1987); Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, Del., 2001).

The sequence encoding an entire variable region of the immunoglobulin polypeptide may be determined; however, it will sometimes be adequate to sequence only a portion of a variable region, for example, the CDR-encoding portion.

Sequencing is carried out using standard techniques. See Sambrook, 1989, supra and Sanger F, et al., Proc. Natl. Acad. Sci. USA 1977; 74:5463-5467. By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md., US.

7. Therapeutic Methods

In another aspect, the invention relates to a method for the treatment or prevention of HIV or AIDS in a subject in need thereof which comprises the administration to said subject of the neutralizing antibodies isolated with the method of the fifth aspect of the invention.

The beneficial treatment or preventive effects of the a neutralizing antibodies HIV in relation to HIV infection or AIDS symptoms include, for example, preventing or delaying initial infection of an individual exposed to HIV; reducing viral burden in an individual infected with HIV; prolonging the asymptomatic phase of HIV infection; maintaining low viral loads in HIV infected patients whose virus levels have been lowered via anti-retroviral therapy (ART); increasing levels of CD4 T cells or lessening the decrease in CD4 T cells, both HIV-1 specific and non-specific, in drug naive patients and in patients treated with ART, increasing overall health or quality of life in an individual with AIDS; and prolonging life expectancy of an individual with AIDS. A clinician can compare the effect of the treatment with the patient's condition prior to treatment, or with the expected condition of an untreated patient, to determine whether the treatment is effective in inhibiting AIDS. In a preferred embodiment, the immunogenic compositions of the invention are preventive compositions.

The neutralizing antibodies of the invention may be useful in the treatment of a HIV-1 infection. While all animals that can be afflicted with HIV-1 or their equivalents can be treated in this manner (e.g. chimpanzees, macaques, baboons or humans), the neutralizing antibodies of the invention are directed particularly to their therapeutic uses in humans. Often, more than one administration may be required to bring about the desired therapeutic effect; the exact protocol (dosage and frequency) can be established by standard clinical procedures.

The present invention further relates to preventing or reducing symptoms associated with HIV infection. These include symptoms associated with the minor symptomatic phase of HIV infection, including, for example, shingles, skin rash and nail infections, mouth sores, recurrent nose and throat infection and weight loss. In addition, further symptoms associated with the major symptomatic phase of HIV infection, include, for instance, oral and vaginal thrush (*Candida*), persistent diarrhea, weight loss, persistent cough and reactivated tuberculosis or recurrent herpes infections, such as cold sores (herpes simplex). Other symptoms of full-blown AIDS which can be treated in accordance with the present invention include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii* pneumonia (PCP), herpes zoster (or shingles), nervous system problems, such as pains, numbness or "pins and needles" in the hands and feet, neurological abnormalities, Kaposi's sarcoma, lymphoma, tuberculosis or other similar opportunistic infections.

In another preferred embodiment, the subject to which the neutralizing antibodies are administered is under antiretroviral therapy (ART), preferably under highly active antiretroviral therapy (HAART).

All publications mentioned herein are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

EXAMPLE 1

Construction of the pcDNA3.1huCD4mIgG1 Plasmid

The D1-D2 N-terminal domains of human CD4 were amplified by standard RT-PCR using the SuperScript III One-Step RT-PCR System with Platinum Taq DNA Pol (Invitrogen Corp., Carslbad, Calif., US) and the following primers:

```
1) CD4 L sense (SEQ ID NO: 1):
5'-CACCATGAACCGGGGAGTCCCTTTTAG-3'

2) CD4L AS NheI (SEQ ID NO: 2):
5'-TATTAGCTAGCACCACGATGTCTATTTTG-3'
```

RNA extracted from human peripheral blood mononuclear cells (PBMC) was used as template. The pcDNA3.1huCD4 plasmid was generated after cloning of the CD4 amplimer using the pcDNA3.1 Directional V5-His-TOPO kit and following the manufacturer's instructions.

The hinge/CH2/CH3 containing-Fc region of murine IgG1 was amplified as it has been previously described using the primers:

```
3) MPER-mIgG1-S (SEQ ID NO: 3):
5'-GAATAGAGCTGGTGGGCTAGCTGTGCCCAGGGATTGTGGT-3'

4) mIgG1-AS (SEQ ID NO: 4):
5'-TTATTCTCGAGTCATTTACCAGGAGAGTGGG-3'
```

As template, RNA extracted from the NS1 murine cell line was used.

The amplimer was purified, digested with the FastDigest NheI and FastDigest XhoI restriction enzymes (Fermentas International Inc., Glen Burnie, Md., US) and ligated into the pcDNA3.1huCD4 (previously linearized with the same restrictions enzymes) using T4 DNA ligase (Fermentas International Inc., Glen Burnie, Md., US). Finally, the DNA-construct integrity was confirmed by sequencing using the BigDye Terminator v3.1 Cycle Sequencing Kit (Applied Biosystems®, Life Technologies Corp., Carlsbad, Calif., US). See SEQ ID NO. 5, SEQ ID NO. 6, SEQ ID NO. 7, and FIG. 1.

EXAMPLE 2

Production of the huCD4mIgG1 Recombinant Protein

HEK 293 cells were transfected with the pcDNA3.1huCD4mIgG1 plasmid using Calphos transfection kit (Clontech®, Takara Bio Inc., Otsu, JP) following the manufacturer's instructions. After 48 hours, the supernatant was collected, clarified by filtration through a 0.45 µm filter (EMD Millipore, Merck KGaA, Darmstadt, Del.) and stored at −20° C. until use.

EXAMPLE 3

Titration of Supernatant Containing the HuCD4mIgG1 Recombinant Protein

Figure 2:
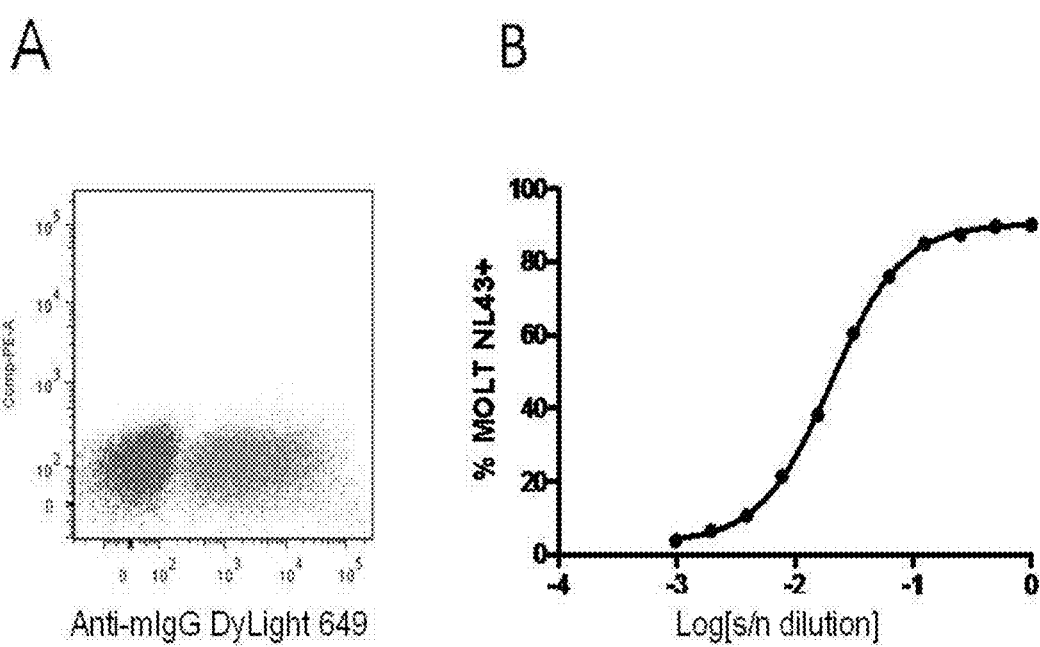
FIG. 2. Titration of HEK 293-supernatant containing the huCD4mIgG1 fusion protein. A) The supernatant of a HEK 293 cell line transfected with the plasmid pcDNA3.1huCD4mIgG1 was used to stain NL4.3 in a chronically infected MOLT cell line. The huCD4mIgG1 protein bound to gp120 on the cellular surface was identified using a DyLight-649 conjugated goat anti-mouse IgG. An uninfected MOLT cell line was used as negative control. B) Titration of the supernatant used to stain the NL4.3 MOLT cell line.

NL4.3 chronically-infected MOLT cell line was incubated with serial dilutions of the CD4mIgG1-containing supernatant for 30 minutes at room temperature. See Blanco J, et al., J. Leukoc. Biol. 2004; 76(4):804-811. After washing with PBS the CD4mIgG1 bound to gp120 on cell surface was detected by flow cytometry using a Fc-specific DyLight 649-F(ab)$_2$ Goat anti-mouse IgG (Jackson ImmunoResearch, Inc., West Grove, Pa., US). See FIG. 2.

EXAMPLE 4

Figure 3:
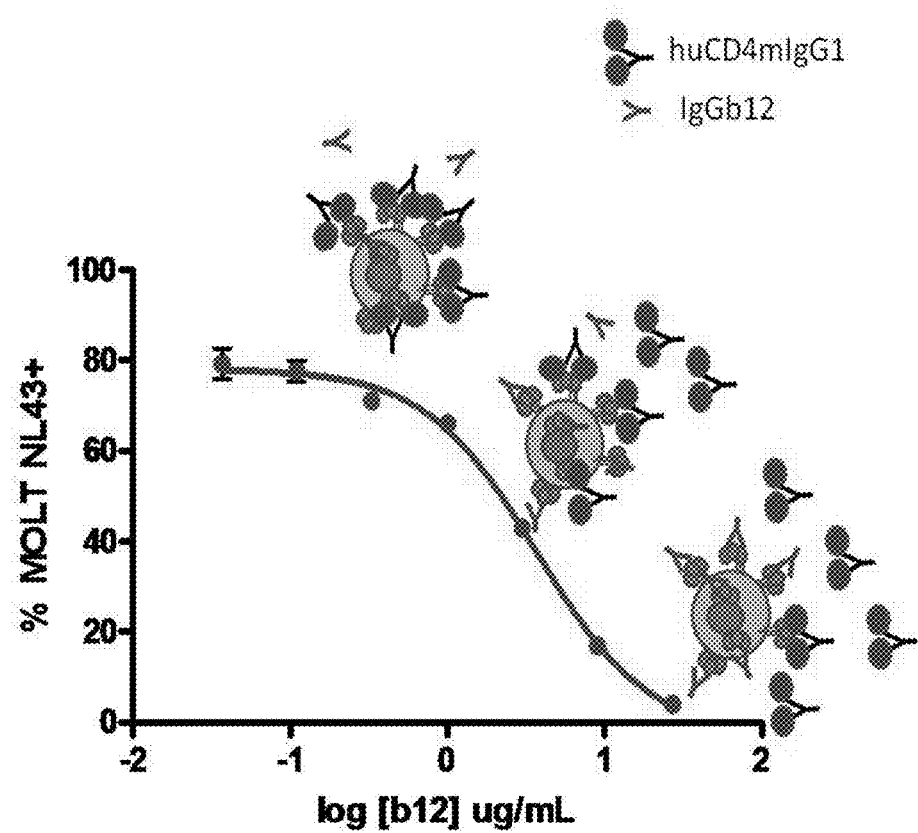
FIG. 3. CD4/gp120 blocking activity of CD4bs-bNAb IgGb12. Titration of the CD4/gp120 blocking activity of the IgGb12 antibody starting at 48 µg/mL was determined. A schematic representation of the mechanism of action of the IgGb12 blocking the interaction between CD4 and gp120 is shown.

Identification of Gp120/CD4 Blocking Antibodies Using a Competitive-Cytometric Assay To determine whether the gp120/CD4 blocking activity of antibodies can be determined by flow cytometry, NL4.3 chronically-infected MOLT cells were pre-incubated at room temperature for 25 minutes with serial dilutions (3 fold) of the IgGb12 antibody, which recognizes the CD4bs of gp120, starting at 48 µg/mL. Then, the HuCD4mIgG1-containing supernatant at IC50 concentration was added and the incubation extended for 30 minutes at room temperature. After two washes with PBS, the secondary antibodies Fc-specific DyLight 649-F(ab)2 goat anti-mouse IgG (Jackson ImmunoResearch, Inc., West Grove, Pa., US) was added and incubated again for 15 minutes at room temperature. The cell samples were washed with PBS and analyzed by flow cytometry. IgGb12 blocked the interaction gp120/CD4 in a quantifiable concentration-dependent kinetics. See FIG. 3.

EXAMPLE 5

Determination of Gp120/CD4 Blocking Specificity

Figure 4:
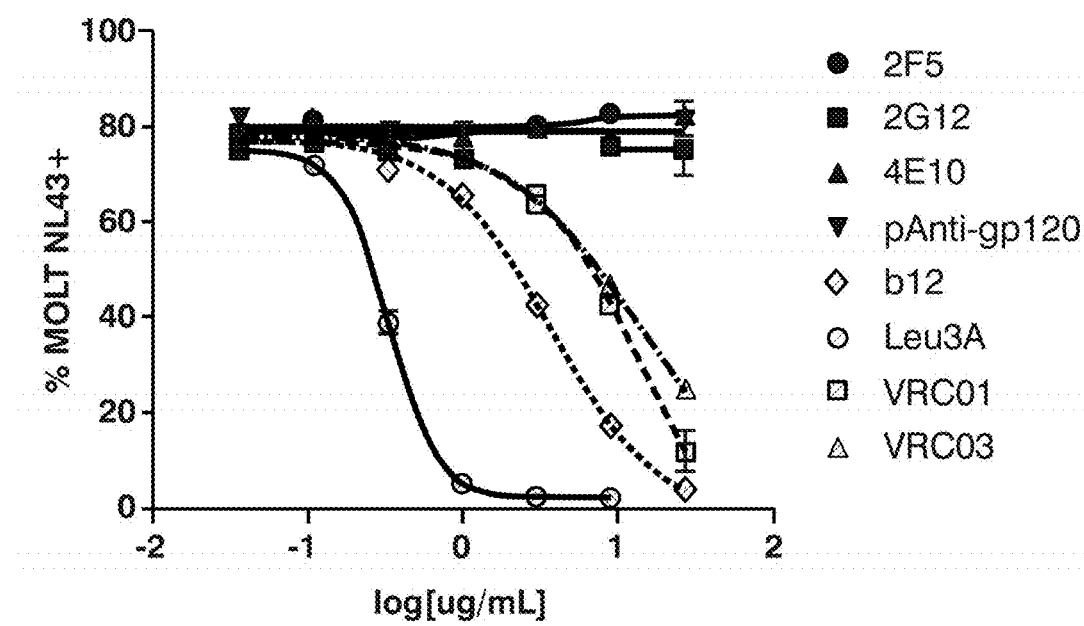
FIG. 4. Relation between the specificity of antibodies and the CD4-gp120 blocking activity. The specificities involved in the CD4-gp120 blocking activity was assayed by utilizing several antibodies which recognized a known set of epitopes in the env glycoprotein. Only antibodies which recognized de CD4bs in gp120 (IgGb12, VRC01 and VRC03) or the gp120bs in CD4 (Leu3a) blocked the interaction between gp120 and CD4, making the assay highly specific for this type of reactivities.

In order to evaluate the specificity of the assay, antibodies which recognized regions in Env glycoprotein other than CD4bs were used in the same conditions described before. See Table 1. Only antibodies which recognized the CD4-binding site in gp120 (IgGb12, VRC01 and VRC03) or the gp120-binding site in CD4 (Leu3a) were able to block the interaction gp120/CD4, indicating that the described assay is highly specific. See FIG. 4.

TABLE 1

Description of the antibodies used to determinate the specificity associated with gp120/CD4 blocking antibodies

| Ab name | Specificity | Source | Description |
|---|---|---|---|
| IgGb12 (b12) | CD4 binding site in gp120 | 1 | human broadly nAb |
| VRC01 | CD4 binding site in gp120 | 2 | human broadly nAb |
| VRC03 | CD4 binding site in gp120 | 2 | human broadly nAb |
| Leu3a | gp120 binding site in CD4 | 3 | mouse Ab |
| IgG2G12 (2G12) | glycosilated epitope in gp120 | 1 | human broadly nAb |
| 2F5 | MPER region in gp41 | 1 | human broadly nAb |

TABLE 1-continued

Description of the antibodies used to determinate the specificity associated with gp120/CD4 blocking antibodies

| Ab name | Specificity | Source | Description |
|---|---|---|---|
| 4E10 | MPER region in gp41 | 1 | human broadly nAb |
| goat anti-gp120 | gp120 | 4 | Non-neutralizing goat polyclonal Ab |

1 Polymun Scientific Immunbiologische Forschung GmbH, Klosterneuburg, AT
2 NIH AIDS Research and Reference Reagent Program, Bethesda, MD, US
3 BD Biosciences Corp., Franklin Lakes, NJ, US
4 Abcam plc, Cambridge, MA, US

EXAMPLE 6

Quantification of Gp120/CD4 Blocking Antibodies in Plasma Samples

Figure 5:
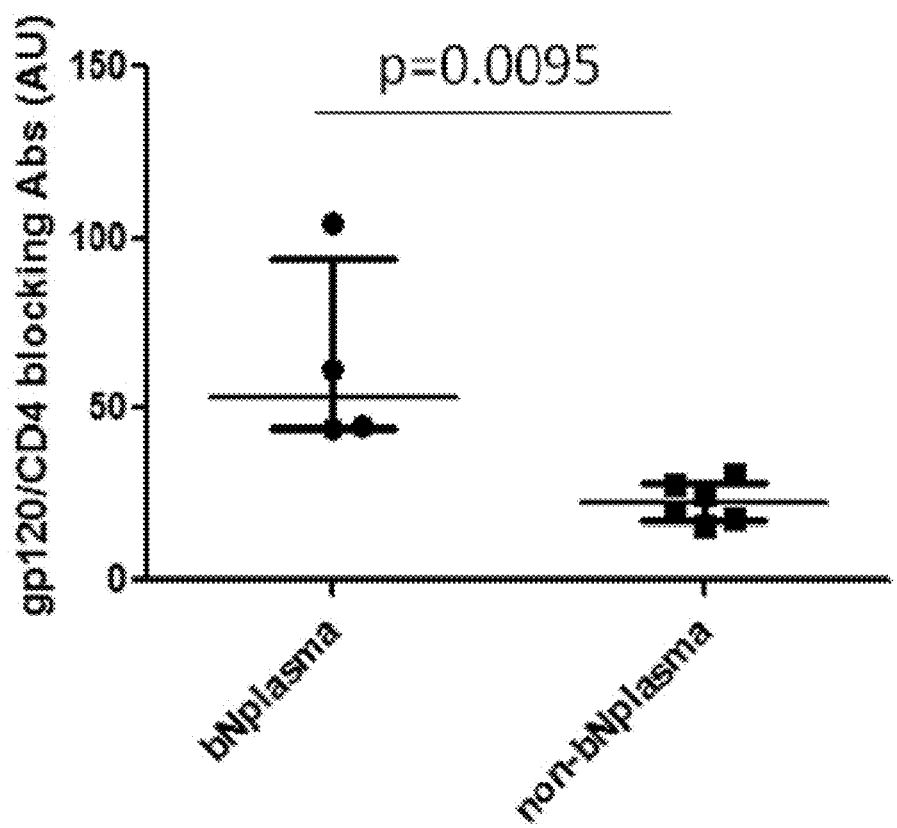
FIG. 5. Quantification of gp120/CD4 blocking antibodies in plasma samples. To determinate the presence of CD4/gp120 blocking antibodies, such as IgGb12, in plasma samples, the CD4/gp120 blocking activity was determined by flow cytometry. A standard curve with IgGb12 was included to quantify the presence of CD4/gp120 blocking antibodies. Broad neutralizing plasma (bNplasma) showed a major presence of CD4-gp120 blocking antibodies than non-bNplasma.

To identify and quantify the gp120/CD4 blocking antibodies in plasma samples and to validate the assay, several plasma samples from HIV-1 infected patients were used. These samples had been previously described and analyzed for their neutralization capacity and for the presence of gp120/CD4 blocking antibodies using a cell-to-cell assay. See Sánchez-Palomino S, et al., Vaccine 2011; 29:5250-5259. A set of four broadly neutralizing plasma samples, which contained gp120/CD4 blocking Abs, and six poorly neutralizing plasmas were analyzed as follows: NL4.3 MOLT cells were pre-incubated with serial dilutions (3 fold, starting at 1/10) of plasma samples for 25 minutes at room temperature. As standard, 3 fold serial dilutions of b12 antibody, starting at 48 µg/mL, were used. Subsequently, the huCD4mIgG1 supernatant was added at IC50 concentration and the incubation period extended for 30 minutes. After washing, the huCD4mIgG1 proteins bound to gp120 on the surface of cells were detected with the Fc-specific DyLight 649-F(ab)2 goat anti-mouse IgG (Jackson ImmunoResearch, Inc., West Grove, Pa., US). Finally, the samples were washed with PBS and analyzed by flow cytometry and the presence of gp120/CD4 blocking antibodies quantified as arbitrary units (AU) related to the b12 antibody used as standard. See FIG. 5.

Figure 6:
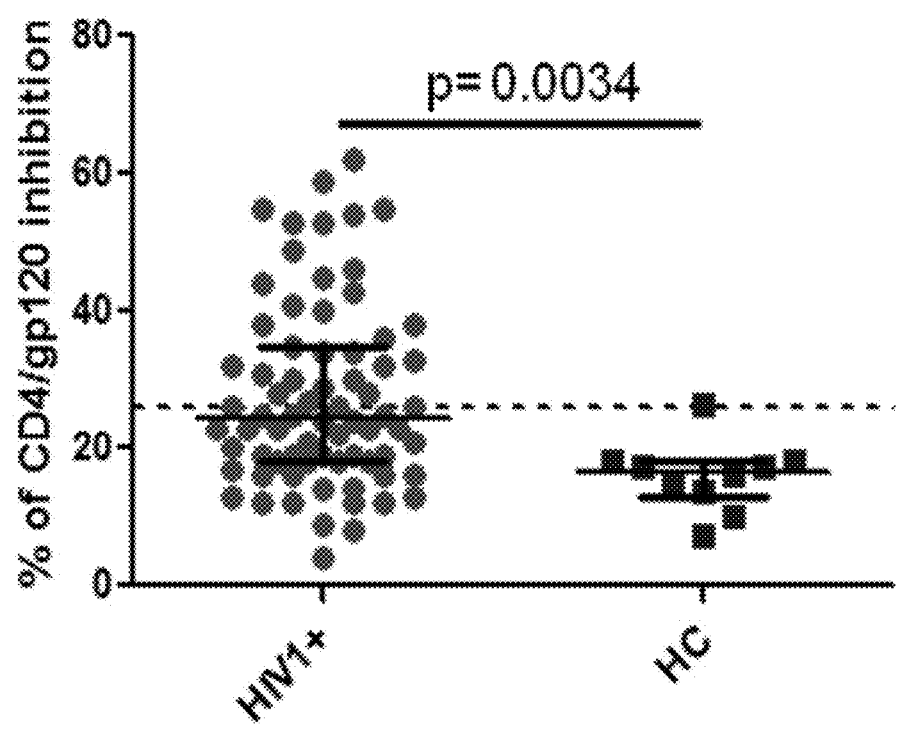
FIG. 6. Quantification of CD4/gp120 blocking antibodies in plasma samples of ART-naive HIV-1 infected patients (HIV-1) and uninfected control individuals (HC). The presence of CD4/gp120 blocking antibodies was tested in 72 plasma samples from HIV-1 infected patients (red circles) and 10 uninfected controls (blue squares). Data show the percentage of CD4/gp120 inhibition. As positive cutoff the median plus two fold standard deviation of uninfected control individuals was fixed. Following this positivity criterion (dashed line), 43% of HIV-1 samples (31 out of 72) and 10% of uninfected control (1 out of 10) were considered as positives (p=0.0034, Mann-Whitney test).

Following the methodology described before, the presence of CD4/gp120 blocking antibodies was tested in a cohort of plasma samples from ART-naïve HIV-1 infected patients and uninfected individuals who were used as negative control. In this case, plasma samples were tested at 1/5 dilution. The results are showed as percentage of CD4/gp120 inhibition. See FIG. 6.

Figure 7:
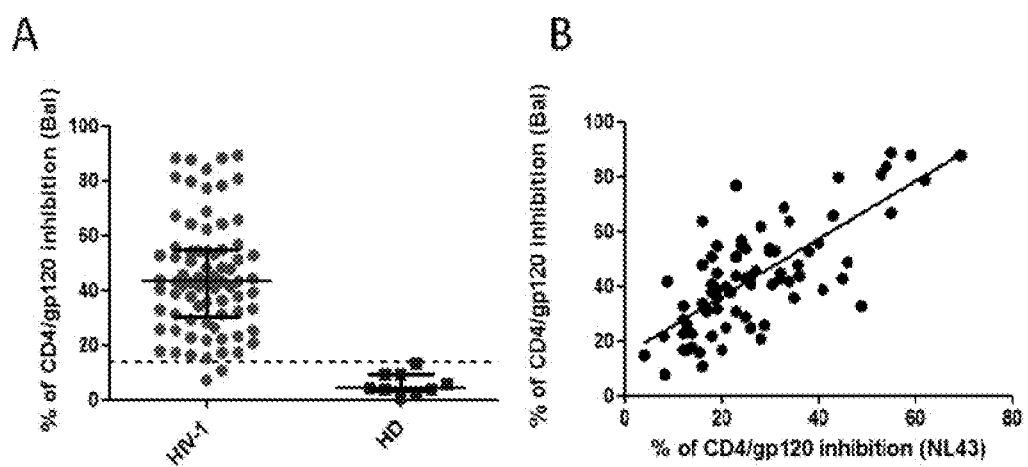
FIG. 7. Quantification of CD4/gp120 blocking antibodies in plasma samples of ART-naive HIV-1 infected patients (HIV-1) and uninfected control individuals (HC) using the HIV-1 isolate BaL.7.A) The presence of CD4/gp120 blocking antibodies was tested in 72 plasma samples from HIV-1 infected patients (red circles) and 9 uninfected controls (blue squares). Data show the percentage of CD4/gp120 inhibition. As positive cutoff the median plus two fold standard deviation of uninfected control individuals was fixed. Following this positivity criterion (dashed line), 97% of HIV-1 samples (70 out of 72) and 0% of uninfected control were considered as positive (p=0.0034, Mann-Whitney test). 7.B) the percentage of inhibition of the binding of huCD4mIgG1 to both NL4-3 and BaL isolates obtained for each plasma sample showed a strong correlation (p<0.0001, Pearson correlation test).

Additional confirmation of the assay was obtained by using an envelope glycoprotein from a different HIV-1 isolate. The same set of plasma samples tested in FIG. 6 was analyzed using MOLT cells expressing the envelope of the HIV-1 Bal Isolate. The results are shown in FIG. 7 and confirm the presence of quantifiable antibodies against the CD4 binding site in plasma from HIV+ individuals. Furthermore, the percentage of inhibition of the binding of huCD4mIgG1 to both NL4-3 and BaL isolates obtained for each plasma sample showed a strong correlation ($p<0.0001$, Pearson correlation test).

The invention claimed is:

1. An in vitro method for determining in a sample HIV neutralizing antibodies which selectively bind to the CD4 binding site of gp120, comprising:
  (i) contacting a cell comprising the CD4 binding site of gp120 on its surface with the sample,
  (ii) adding a fusion protein comprising (i) a protein capable of selectively binding to the CD4 binding-site of gp120 and (ii) a Fc region of a primary antibody, and
  (iii) measuring, by flow cytometry, the binding efficacy of the fusion protein to the CD4 binding site of gp120,
wherein said HIV neutralizing antibodies are determined to be present in the sample if the binding of the fusion protein to the CD4 binding site of gp120 is inhibited in the presence of the sample, wherein the primary antibody is a non-human IgG or a functionally equivalent variant and wherein the HIV neutralizing antibodies recognize the CD4-binding site in gp120.

2. The method of claim 1, wherein the protein capable of binding to the CD4 binding-site of gp120 is CD4 or a functionally equivalent variant thereof.

3. The method of claim 1, wherein the functionally equivalent variant of CD4 is a CD4 fragment comprising at least the D1-D2 N-terminal domains of CD4.

4. The method of claim 1, wherein the measuring comprises using a reporter binding to the fusion protein.

5. The method of claim 1, wherein the cell is a HIV-infected cell, and wherein the HIV-infected cell is preferably chronically infected.

6. The method of claim 1, wherein step (ii) is preceded by at least one washing step removing unbound fusion protein.

7. The method of claim 1, wherein the determination is a quantitative determination.

8. The method of claim 1, wherein the sample is a plasma sample.

9. The method of claim 1, wherein the non-human IgG is a murine IgG.

10. The method of claim 9, wherein the murine IgG is murine IgG-1.

11. An in vitro method for the identification of an antibody-producing cell expressing HIV neutralizing antibodies, comprising:
  (i) contacting a cell comprising the CD4 binding site of gp120 on its surface with a supernatant of a culture of the antibody-producing cell and with a fusion protein comprising (i) a protein capable of selectively binding to the CD4 binding-site of gp120 and (ii) an Fc region of a primary antibody, and
(ii) measuring the binding efficacy of the fusion protein to the CD4 binding site of gp120, wherein the antibody-producing cell are determined as expressing HIV neutralizing antibodies if the binding of the fusion protein to the CD4 binding site of gp120 is inhibited in the presence of the supernatant, wherein the primary antibody is a non-human IgG or a functionally equivalent variant and wherein the HIV neutralizing antibodies recognize the CD4-binding site in gp120.

12. A method for producing HIV neutralizing antibodies, comprising:
(i) culturing antibody-producing cells isolated according to claim 11 and
(ii) isolating the antibodies expressed by the antibody-producing cells.

13. The in vitro method of claim 12, wherein the non-human IgG is a murine IgG.

14. The method of claim 13, wherein the murine IgG is murine IgG-1.

\* \* \* \* \*

UNITED STATES PATENT AND TRADEMARK OFFICE
CERTIFICATE OF CORRECTION

PATENT NO. : 9,952,218 B2
APPLICATION NO. : 14/426235
DATED : April 24, 2018
INVENTOR(S) : Julián Miguel Blanco Arbués and Jorge Carrillo Molina It is certified that error appears in the above-identified patent and that said Letters Patent is hereby corrected as shown below:

On the Title Page

Column 2, under OTHER PUBLICATIONS, Line 8; "Anthony" should read -- West --

Page 2, Column 2, under OTHER PUBLICATIONS, Line 30; "896-661" should read -- 856-861 --

In the Claims

Column 34, Line 45: "Claim 1" should read -- Claim 2 --

Signed and Sealed this
Twenty-sixth Day of June, 2018

Andrei Iancu
*Director of the United States Patent and Trademark Office*